US005978804A

United States Patent [19]
Dietzman

[11] Patent Number: 5,978,804
[45] Date of Patent: Nov. 2, 1999

[54] NATURAL PRODUCTS INFORMATION SYSTEM

[76] Inventor: Gregg R. Dietzman, 180 First St., Friday Harbor, Wash. 98250

[21] Appl. No.: 08/833,915

[22] Filed: Apr. 10, 1997

Related U.S. Application Data

[60] Provisional application No. 60/015,286, Apr. 11, 1996.
[51] Int. Cl.$^6$ ......................................... G06F 17/30
[52] U.S. Cl. .............................. 707/10; 707/104
[58] Field of Search .......................... 707/10, 100, 104, 707/103

[56] References Cited

U.S. PATENT DOCUMENTS

| | | | |
|---|---|---|---|
| 5,179,652 | 1/1993 | Rozmanith et al. | 345/331 |
| 5,241,671 | 8/1993 | Reed et al. | 707/104 |
| 5,553,277 | 9/1996 | Hirano et al. | 707/104 |
| 5,745,895 | 4/1998 | Bingham et al. | 707/10 |
| 5,781,773 | 7/1998 | Vanderpool et al. | 707/100 |

OTHER PUBLICATIONS

Duncan, "Publishing Databases on the World–Wide Web", PC Magazine pp. 403, 406–408, 410, and 412, Aug. 1995.

*Primary Examiner*—Jack M. Choules
*Attorney, Agent, or Firm*—Seed and Berry LLP

[57] ABSTRACT

Disclosed is a data processing system for processing natural product information entered into the system using a standardized entry protocol. The data processing system stores data such as chemical structures, geographic locations, taxonomy, genus synonyms, and textual descriptions and related natural products images such as images of the organisms, and geographic maps. The natural product images are correlated with the natural products data to allow display of the images with the related data. The data processing system further correlates the data products data and images stored in the system with remote databases, such as those containing existing commercially available data, linking the remote data thus correlated for display.

12 Claims, 28 Drawing Sheets

POINTS/POLYGONS
Collection sites
Range of species occurrence
Salinity boundary
Forest stand type
Cultural boundary

NETWORKS/LINES
Shoreline
Rivers
Railway

RASTERS (=pixels)
Aerial photos
Remote sensing

Terrestrial Collection Data Record

File   Edit   Record   Help

Taxonomy | Biology/Ecology | Sample | Voucher | Ethnobotany | Control | Photos

Collection No: W199604050102 # of samples for this collection: 2

Sample No: 2-005    Hazard: None

Taxonomy

KINGDOM:   PLANTAE
PHYLUM:    MAGNOLIOPHYTA
CLASS:     MAGNOLIOPSIDA
ORDER:     HAMAMELIDALES
FAMILY:    CERCIDIPHYLLACEAE
GENUS:     CERCIDIPHYLLUM
SPECIES:   JAPONICUM
COMMON:

Organism Part: Flower

Bulk Sample
Initial Wet Weight (g): 1000
Container: plastic bag
Status: Dry
Storage: Drawer 51
Remaining Bulk Material: 700   wet wt (g)

Ground Sample
Wet Weight (g): 0
Container: plastic bag
Status: Frozen
Storage: Freezer 24
Remaining Ground Material: 0   wet wt (g)

Total Sample Material Remaining (g): 700

Sample Submittal...

Terrestrial Collection Data Record

File  Edit  Record  Help

Taxonomy | Biology/Ecology | Sample | Voucher | Ethnobotany | Control | Photos | Site | Chem Collection No: W199604050102 # of vouchers taken: 6

Taxonomy
- KINGDOM: PLANTAE
- PHYLUM: MAGNOLIOPHYTA
- CLASS: MAGNOLIOPSIDA
- ORDER: HAMAMELIDALES
- FAMILY: DIDYMELACEAE
- GENUS: DIDYMELES
- SPECIES: INTERGRIFOLIA
- COMMON:

# of vouchers remaining: 3

Curation
- Type No: 96-80142

Voucher Archive
- Container: cardstock
- Status: Dry
- Storage: museum

Voucher Sumittal...

Fig. 6K

| Transmittal_ID | Transmittal_Item | Site_ID | Collect_ID | Sample_ID | Phylum | Micro_Sou |
|---|---|---|---|---|---|---|
| 46972 | 1 | W199604230 | W199604230101 | M-001 | PORIFERA | |
| 46972 | 2 | W199604230 | W199604230101 | M-002 | PORIFERA | |
| 46972 | 3 | W199604230 | W199604230102 | M-003 | PORIFERA | |
| 46972 | 4 | W199604230 | W199604230102 | M-004 | PORIFERA | |
| 46972 | 5 | W199604260 | W199604260101 | M-005 | CHORDATA | |
| 46972 | 6 | W199604260 | W199604260102 | M-006 | PHAEOPHYCOPHY | |
| 46972 | 7 | W199604280 | W199604280101 | M-007 | CNIDARIA | |
| 46972 | 8 | W199604280 | W199604280101 | M-008 | CNIDARIA | |
| 46972 | 9 | W199604260 | W199604260103 | M-009 | RHODOPHYCOTA | |
| 46972 | 10 | W199604280 | W199604280102 | M-010 | PORIFERA | |
| 46972 | 11 | W199604280 | W199604280102 | M-011 | PORIFERA | |
| 46972 | 12 | W199604280 | W199604280102 | M-012 | PORIFERA | |

Field Tissue Sample Submittal - Submittal: 46972

File Edit Record Submit Help

Date: 28 Oct 1998
Transmittal ID: 46972
Records: 21
Samples: 21
Collections: 11

Submit To:
Company: The Upjohn Company
Department: Chemistry
Contact: Charles Spelman, PhD
Street: 200 Portage Road
City: Kalamazoo   State: MI   Zip: 49001
Phone: 616/385-7358

Pie Chart
Site Map
Set Values
SUBMIT

Collection   Site

NATURAL PRODUCTS INFORMATION SYSTEM

This application claims benefit of provisional Application Ser. No. 60,015,286 filed Apr. 11, 1996.

TECHNICAL FIELD

The present invention pertains to a computer-implemented system for managing a configuration of natural products inventory, and, more particularly, to an integrated computer database system for the processing of information on natural product chemistry, biological activity, and biodiversity to enable the creation of custom taxonomic schemes, photographic and scanned laboratory print-out image handling, and interfacing with remote databases, including a geographical information system and global positioning system.

BACKGROUND OF THE INVENTION

Most drug discovery programs are based on the "empirical" drug development approach where large numbers of substances are screened for activity against a panel of assays that target a therapeutic group. Inclusion of natural products in this approach is problematic because of two issues—dereplication and recollection. Dereplication is important in a program where the number of assays is small and the number of natural products source organisms is large, where the goal is to avoid processing the same organism (from the same site) twice or discovering known compounds from new sources. Collecting the same organism from different geographical regions, however, is appropriate because of the differences in secondary metabolite production by the same organism from different habitats. Integrating chemistry and biological activity data is also important when applying the "empirical" drug development approach for defining models felt to be of predictive use. These technical issues are often the effective core of collection guidance in an acquisition program.

Dereplication and recollection of source organisms must be addressed in a high throughput acquisition program. Both issues require comprehensive information management. These are related issues because they require a similar technical approach—both have a spatial feature. Expedition planning requires application of information on past collections, to know what was collected where. Recollection is a less complicated issue; however, to recollect from the same or identical site is critical for scale-up.

Dereplication by chemotaxonomy is also useful to natural products investigators. The identification of "nuisance" compounds, those which show positive results in a bioassay but are not considered potential drugs is critical in drug discovery programs utilizing bioassay guided bioassay schemes. For example, detergents, salts, and chemical classes known not to be of interest but without defined structures such as polysaccharides in anti-HIV assays and polyphenolics in anti-viral assays. Also, rapid identification of known compounds that have been previously tested and no longer of interest, increases the efficiency of bio-assay guided isolations. For example, the discovery of the inhibitory effect of quercetin against a protein-tyrosine kinase (PTK) triggered a thorough study of the activity of flavonoids as PTK inhibitors. If new compounds are sought with PTK inhibitory activity that are not flavonoids, an effort must be made to dereplicate the flavonoid substructure.

Field identifications are an invaluable tool in dereplication by chemotaxonomy. The availability of easily accessible on-site photographs, organism descriptions, and distribution information is critical to field identifications. In some cases identification down to only the family or order level can be helpful to a researcher. For example, a chemist working with a sponge that was identified in the field as belonging to the order Vergonida should expect to find bromotyrosine derivatives.

These information management requirements, however, can become assets that are used to guide the collection effort and enhance the probability of success. Screening natural products extracts does not necessarily require a random approach. Examples of structure/activity relationships are beginning to emerge for a variety of biological assays. Published information on marine natural products chemistry and related biological activity can guide a collection effort to target, but not duplicate collections from, organism groups with known properties. This targeting relates to the efforts of Shaman Pharmaceuticals, a drug discovery company that collects plant samples based on confirmed ethnobotanical features. Clearly, a contemporary high throughput drug development program requires advanced capabilities for information handling.

The global Internet has changed fundamental aspects of the way scientists work. Electronic mail and a variety of other data exchanges provide researchers with extended capabilities that set the tone and pace of many collaborative investigations. On-line services provide ready access to scientific journals and specialty databases. "The Internet is one of the absolutely critical tools for modern biology. Biological research will become increasingly dominated by the exchange of large amounts of information and by cooperative work on large amounts of information. And the only way to support that is through the networks" (Fields, 1994). Internet-based multimedia technologies are again extending the capability for scientific collaboration.

The Internet provides a unique forum for dissemination of biological information. However, bulletin board services (BBS) and workgroups cover such a wide spectrum that it is difficult to filter a subset of appropriate information. Many users become frustrated by not only the amount of electronic mail they have to sort, but also by the number of non-refereed information sources that they must consider. Database projects on a broader scale are fragmented and their coordination is an immense task. Indeed, the National Biological Information Infrastructure (NBII), currently under development by the National Biological Survey, is a federal-level project that seeks only to provide identification of and route access to biological information.

The present invention, known as natural products Information System (NAPIS) provides an effective solution to the extended requirements for screening natural products. Combining dereplication and recollection with expedition planning turns the requirements for information handling into assets that enhance the probability of success. NAPIS technology is appropriate for natural products drug discovery efforts at the large-scale level, the university laboratory level, and the independent collector level. Biodiversity inventory projects, taxonomists and environmental conservation groups will also find NAPIS system features that are appropriate for support of their efforts.

SUMMARY OF THE INVENTION

The present invention is directed to a computer-implemented system for processing natural product information. The natural product information includes, but is not limited to, natural products data and natural products images. For example, the data can include chemical structures, geographic locations, textual data, taxonomy, genus synonyms, taxonomic classifications, etc. Natural products images will include, but are not limited to, images of organisms from photographs, slides, and video, as well as geographic maps, tables, charts, and the like.

In accordance with the present invention, the system comprises a computer processor for processing data; memory for storing data on a storage medium; a display device for displaying data; means for processing natural products data preferably in a standard format; means for processing natural products images and correlating the natural products images with the natural products data; and means for correlating the natural products data and natural products images with remote databases to form correlated data for storage in the memory and for display to a user on the display device.

In accordance with another embodiment of the invention, a dataprocessing system for managing a configuration of natural products inventory is provided. The system comprises a computer processor for processing data; a storage device for storing data; means for processing natural products data, ideally in a standard format; means for processing natural products image data and correlating the natural products image data with the natural products data; and means for correlating data regarding the natural products image data and the natural products data with remote databases.

In accordance with yet another aspect of the present invention, the means for correlating with remote databases further includes means for correlating the natural products data with a taxonomic structure.

In accordance with yet a further aspect of the present invention, the correlating means further includes a graphical user interface and, optionally, an interface with the geographic information system.

In accordance with a further aspect of the present invention, the correlating means is configured to correlate the natural products data and the natural products image data with geographical information systems. Ideally, the correlating means is further configured to correlate the remote databases based on one of either a genus species identification, Chemical Abstracts Registry Number, or the National Oceanographic Data Center Taxonomic Code or Serial No.

In accordance with still yet a further aspect of the present invention, the second means for processing natural products image data includes handling of digital images.

As will be readily appreciated from the foregoing, the present invention provides a unique system for processing information regarding natural products from around the world. This system uses advanced technologies to provide a standard for data capture and exchange. The key features include interface with commercially-available databases through a phylogenetic structure database engine (PSDE) that forms a part of the present invention, the ability to easily create custom taxonomic schemes, photographic and scanned laboratory print-out image handling, and a geographical information system (GIS) that is tailored to the needs of natural products investigators and biodiversity inventory projects. Project managers will use the system as an interface to bridge the gap between the library, the laboratory, and the field. Natural products development and biodiversity inventory projects will use NAPIS as a frontline method for effective control of their laboratory and field efforts, and as a forum for information exchange on the Internet.

BRIEF DESCRIPTION OF THE DRAWINGS

The foregoing and other features and advantages of the present invention will be more readily appreciated as the same become better understood from the following detailed description when taken and in conjunction with the accompanying drawings, wherein.

DETAILED DESCRIPTION OF A REPRESENTATIVE EMBODIMENT

I. Introduction

Figure 1A:
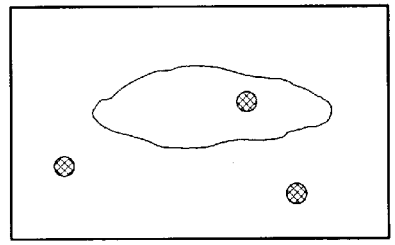
FIGS. 1A–C are representations of various forms of spatial data.

The present invention is directed to matching currently-available computer technologies with natural products investigators who track collections, plan expeditions, and prioritize active leads. The inventor's prior-filed U.S. provisional application, Ser. No. 60/015,286, is incorporated herein by reference.

The trends in high throughput screening technology, in addition to computer technology, are toward faster, smaller, and less expensive. This results in the capability to evaluate a large number of test substances against multiple therapeutic targets. Synthetic and combinatorial chemistry methods now provide most of the chemical diversity presented to drug discovery screens, however, where natural products represent even a fraction of the total, the information handling requirements are significant.

Information handling for natural products acquisitions is different from laboratory information management. Each involves tracking samples through different processes, but natural products chemicals are acquired from biological sources that are both phylogenetically and geographically diverse. Computer technologies can now link photographs of these diverse biological specimens (some new to science) to traditional database records, and to place their geographic positions on an associated computer map. Traditional database queries can then be extended to include a spatial element using geographic information system (GIS) technology. Information on known natural products chemistry from outside sources can also be linked to a GIS.

Natural products investigators must address the issues of sample recollection and dereplication, and can now use computer technologies to effectively meet these requirements. Furthermore, the knowledge base developed over years of natural products investigation can be linked between computer databases to reveal organism group/chemical structure/biological activity relationships, for use in guiding future efforts.

A. Specific Features

NAPIS (natural products Information System) is a computerized database system concept for supporting natural products investigators worldwide. NAPIS provides a standard data format that allows for efficient dissemination of natural products information. NAPIS has two main features: integrated sample collection, chemical and biological activity data, and an interface to existing commercially available data. Project managers will find it useful as an interface between their projects and existing academic, industry, and natural feature spatial data (maps).

1. Dissemination of Information. NAPIS is an information exchange service for natural products chemists and drug discovery efforts worldwide, and extend the system to manage information on marine organisms, terrestrial plants and microbial organisms. The NAPIS Core system contains the software program application and serve as the information repository. Users can exchange information across the Internet.

2. Standardize Data Capture and Exchange Methods. NAPIS Laboratory is a supported software module that enables users to capture and manage natural products acquisition, chemistry and biological activity data whereas traditional text-field data are linked to digitally stored images including chemical chromatography and spectroscopy profiles and organism photographs. This allows investigators to refer to profiles on the core system and compare results, or to compare organism photographs. NAPIS Remote is a module for use in the field by natural products source material collectors. Both modules will interface with the NAPIS Core.

3. Amplified Phylogenetic Structure Database Engine (PSDE). This process updates the taxonomic "standard checklist" and its linkage to the geographical information system (GIS)-based "range of species occurrence", provides the capability to "graphically" generate custom taxonomy using "click and drag" methods, and provides further access to commercially-available chemistry and biodiversity databases.

Using graphical user interface technologies, NAPIS software design provides users with intuitive "menu driven" navigation through the system, resulting in a heightened sense of orientation. Many nongraphical user interfaces to data are disorienting to the users. The NAPIS menus and data entry forms all have the same "look and feel" so the user knows what to expect; these same standards are applied to all the modules. Data capture is rapid, effective and relatively error-free. Text data are, in many cases, entered using "menu picks" from a "pull down" menu that contains default choices-there is no text entry into these fields, and no typographical errors. NAPIS also forces entry in standard format, two examples are entry of date as month/day/year, and entry of geographical position as degrees/minutes/seconds (and not degrees/minutes/tenths of minutes); these two features alone solve the majority of problems encountered by the National Cancer Institute when they receive information from contract collectors. Images of organisms from photographs, slides and video can be captured and managed by the system, and are displayed in low-resolution format on the screen-form. True-color photo-real images can be printed. Non-computer image management requires greater space, image quality degrades over time, and information in this is generally not available in the field. Scanned images can be captured while entering other data on chemistry work-up. This allows investigators the ability to view chromatography and spectroscopy results for chemical characterization on-screen. This same technology can be applied to biological activity testing. Image data are linked to text records and are ready for rapid exchange within NAPIS and throughout the Internet.

a. Standardized Data Exchange

To communicate with other databases NAPIS uses linkage on genus species name, Chemical Abstracts Registry Number, or the National Oceanographic Data Center (NODC) Taxonomic Code. While data format inconsistencies exist between systems and create problems for efficient data exchange, NAPIS is designed using standards which provide for data consistency within the system and for clean connection with major databases. For example, database linkage on genus species name is problematic because exact matches are required, any typographical error causes a matching error, and the data comparisons to determine a match are case sensitive. To address this issue, the NAPIS PSDE uses a the NODC Taxonomic Code, a widely distributed checklist of organism names. The NODC Taxonomic Code is a numbering system assigned to organisms, was entered and checked for errors, all entry is in upper case and is used by many database projects. In consideration for data exchange, NAPIS standard data entry of organism names uses the NODC-based PSDE tables to present users with "menu pick" choices. While the NODC Taxonomic Code is primarily marine, it was recently extended to also contain information on terrestrial organisms through US Geological Survey activities; the dataset will be further expanded under the administration of the National Biological Survey.

b. PSDE (Phylogenetic Structure Database Engine)

The PSDE seeks to provide structure to genus species lists that are obtained from outside sources where phylogeny, as reflected in taxonomy, is the first-choice method for grouping like organisms.

Most existing databases include a genus species field but do not include family and order, and many do not even contain Phylum information. The utilization of these databases requires knowledge of taxonomy, genus synonyms, as well as all possible family/order classifications. As an example, a researcher working on a sponge of the genus Xestospongia would need to know that since 1977 this genus has been classified in four different ways: family Nepheliospongiidae, order Nepheliospongida; Family Petrosiidae, order Haplosclerida; family Petrosiidae, order Petrosida; and family Nepheliospongiidae, order Haplosclerida. The PSDE will incorporate the multiple classification schemes such as those published for Xestospongia, arming a researcher with an in-depth knowledge of an organism without having to wait for consultation from an expert. The PSDE will also allow investigators to create custom taxonomy using easy "graphical" interface "click and drag" methods. NAPIS also includes synonyms and common names.

The PSDE will take genus lists from any source and apply a taxonomic structure, which reflects phylogeny, or an alternative structure, to them. Multiple classification schemes can be readily applied such as chemotaxonomy, cladistics, or unresolved disputes over classification. The PSDE will allow investigators flexibility when looking for trends within a complicated hierarchical structure.

c. Geographical Information System GIS

GIS is a database management technology that relates cartographic, or spatial data, with very large sets of related information. The list of GIS applications is extensive; one notable application is tracking the impact of Hurricane Andrew in Florida. The initial damage assessment was followed with updates of the recovery effort. Mapped street, utility, parcel, and natural feature information were integrated with written text, and video images taken from helicopters. GIS allowed for the rapid and comprehensive handling of this extensive and dynamic data set.

NAPIS will provide GIS technology to natural products investigators and biodiversity inventory projects on a specific and appropriate level. Scientists are sometimes frustrated by full-featured GIS products that require years to become proficient at. The NAPIS design provides a custom interface that gives biologists selective access to high-end GIS.

Appropriate base-map data are required for the different applications. Natural products investigators only want to see points on a grid as related to a topographical map for planning collections. Biodiversity inventory projects will desire use of the new aircraft and satellite-base multichannel spectralscanning technologies that allow for accurate image processing of natural resource data. Also, both sets of base-map data will have to be rectified to a coordinate base requiring survey control. NAPIS is compatible with satellite-based geographical position system (GPS) technology that will return a latitude-longitude position.

B. Information Handling System General Requirements

When one of the test substances registers as a confirmed "hit" in a discovery screen, the people involved simply want to know: what is it, where did it come from, is it novel and how to get more. The general system requirements, therefore, fall into two categories:

recollection, dereplication.

Recollection must be a cornerstone of any natural products acquisition program; you must be able to go back and get more of the source organism for follow-on studies—it is a simple but critical element. Dereplication against the growing number of known chemical compounds is becoming increasingly important for discovery screens. Based upon initial chemical characterization of an active fractions, a chemical substructure-based database search can be performed to compare with, and dereplicate against, known chemical compounds. Laboratory chemists are at a tremendous advantage when they can generate a list of possible chemical structures to compare with an extract containing unknown compounds. A chemist can then quickly evaluate the possibility for the presence of known compounds and will be able to make an informed decision regarding the interest in the extract as a source of novel bioactive compounds. This rapid process can save the costs of follow-on isolation and structural elucidation studies and increase a program's efficiency.

Dereplication by chemotaxonomy is also useful to natural products investigators. The identification of "nuisance" compounds, those which show positive results in a bioassay but are not considered potential drugs, is critical in drug discovery programs utilizing bioassay guided bioassay schemes]. For example, detergents, salts, and chemical classes known not to be of interest but without defined structures such as polysaccharides in anti-HIV assays and polyphenolics in anti-viral assays. Also, rapid identification of known compounds that have been previously tested, and are no longer of interest, increases the efficiency of bio-assay guided isolations. For example, the discovery of the inhibitory effect of quercetin against a protein-tyrosine kinase (PTK) triggered a thorough study of the activity of flavonoids as PTK inhibitors. If new compounds are sought with PTK inhibitory activity that are not flavonoids, an effort must be made to dereplicate the flavonoid substructure.

The rapid identification of known nuisance compounds can be approached in several ways. Providing research chemists who perform bioassay-guided isolations with a sample identified as close to genus level as possible can provide a general idea as to the chemistry of the organism. This, of course, relies on the availability of a database like NAPRALERT which is available through Scientific and Technical Network (STN), or university specialty group databases that correlate the identification of the source organism to compound structures.

The system general requirements are recollection and dereplication. These requirements share a common feature: they both have a spatial, or mapable, element. The latitude-longitude location of a source organism collection can be easily obtained using satellite navigation technologies and placed on a map. The position of past collections can be similarly mapped, however, the accuracy of these data will vary. It is possible to map these positions in a geographic information system (GIS) where computer-based mapped data are linked to traditional text/field database records. Using a comprehensive dataset of natural products chemical discoveries within a GIS would allow investigators to easily visualize the spatial relationships between collection points to support decisions. Furthermore, expeditions for new acquisition efforts could effectively be planned to target specific regions based on existing information, and to avoid duplicating past collections.

C. Available Computer Technology

Computer technologies now exist to meet the information handling requirements of natural products acquisition programs. While these requirements involve a variety of computer technologies, it is possible to represent the users' view when developing computer applications. This contrasts past computer application development by making the technologies easier to understand and eliminating the requirements for computer specialists in position between the computer and the user. Standards are emerging for a variety of computer software functions and users generally know what to expect from computer capability.

The rapid pace of computer technology development is toward faster, better and smaller systems. Many computer software functionalities are now embellished to levels where they offer a comprehensive set of capabilities. While computer systems are increasingly powerful, they are obsolete at the time they are delivered. One of the difficulties in implementing a fully-featured computer database project is selection of starting materials such as hardware, software and the operating system. It is generally considered best to implement projects on stable hardware and software platforms and not try to anticipate trends (e.g., operating system development) that the industry may follow. This approach is based upon using the existing versions of software development tools, it avoids delays in release of future versions and insures version compatibility with other software, hardware or device drivers used in the project. The dynamic and uncertain elements of computer industry trends notwithstanding, computer hardware technologies now offer a level of power and operability that makes high-end software applications available in portable field units. Furthermore, network connectivity is also now available using a variety of methods.

The global Internet has changed fundamental aspects of the way scientists work. Electronic mail and a variety of other data exchanges provide researchers with extended capabilities that set the tone and pace of many collaborative investigations. On-line services provide ready access to scientific journals and specialty databases. "The Internet is one of the absolutely critical tools for modern biology. Biological research will become increasingly dominated by the exchange of large amounts of information and by cooperative work on large amounts of information. And the only way to support that is through the networks". Internet-based multimedia technologies are again extending the capability for scientific collaboration.

The Internet provides a unique forum for dissemination of biological information. However, bulletin board services (BBS) and workgroups cover such a wide spectrum that it is difficult to filter a subset of appropriate information. Many users become frustrated by not only the amount of electronic mail they have to sort, but also by the number of non-refereed information sources that they must consider. There are many related database projects that are under development on parallel tracks. Database projects on a broader scale are fragmented and their coordination is an immense task. Indeed, the National Biological Information Infrastructure (NBII) currently under development by the National Biological Services (but with uncertain funding), is a federal-level project that seeks only to provide identification of and route access to biological information. An important element of the NBII is to develop "metadata" standards, data that describe the identified data Metadata are especially important for spatial data (=maps) because they describe the accuracy of mapped features.

D. Chemical Prospecting/Biodiversity Inventory

Chemical prospecting, or sometimes called biodiversity prospecting, is the terminology used to describe "the exploration of biodiversity for commercially valuable genetic and biochemical resources". Biodiversity inventory is an essential first step and the issues are linked to the topic of information handling for natural products acquisitions. Access to chemical diversity not only requires acquisition of source organism tissue samples but also requires a permit to collect them. Using computer technologies to plan an acquisition program also provides a basis for the effective communication of these plans to organizations that control the natural resources. In addition, tracking these collections provides the information necessary to monitor progress and insure that the activities are indeed sustainable. Information handling technology has value as a stewardship tool within the structure of international collaborations for transfer of biodiversity resources to industry.

In simple terms, initial stages of the decision-making process involve a review of the resources and their current uses. Later stages consider the impacts and sustainability of proposed resource extraction activities and may track these activities with monitoring programs. Communicating ideas based upon supporting resource information is best done using maps. The conceptual information that maps present is sometimes referred to as deep-structure information and is defined as "geographical relationships as a part of spatial context and meaning". In addition, surface structure information, symbols and clusters of symbols, is a primary level of mapped information. Together they support the decision-making process for geographical problem solving. Computer mapping and database applications are combined within a geographic information system (GIS), and provide an effective means for data management, analysis and presentation.

E. Summary

High throughput screening is an information-intensive discipline. The breadth of existing information that is necessary to consider in the discovery process, the increasing number of samples submitted for testing and the evolving discovery screen models all contribute to a growing dataset. Whatever the application, information handling requirements will grow. Currently available technologies can meet the information handling requirements for natural products acquisition programs. These technologies, however, must be effectively realized for an application. For example, GIS technology is a powerful tool that is typically delivered with extended capabilities that reach beyond the described general requirements for this application. In developing an effective solution, the GIS capability must be delivered in a customized format that provides only those features needed by the natural products investigator-again, this and other technologies must be realized for the application.

These information management requirements, however, can become assets that are used to guide the collection effort and enhance the probability of success. Screening natural products extracts does not necessarily require a random approach. Examples of structure/activity relationships are beginning to emerge for a variety of biological assays. Published information on natural products chemistry and related biological activity can guide a collection effort to target, but not duplicate collections from, organism groups with known properties. A contemporary drug discovery program requires advanced capabilities for information handling.

To accomplish the general requirements of recollection and dereplication, the key features of a comprehensive information management system must include:

link to commercially-available databases link to digitally-stored specimen photographs standardized entry protocols GIS (geographic information system) functionality The goal of any information management system that supports natural products investigators is to provide these technologies in a computer application that is both powerful and easy to use.

An essential first step for information handling for natural products acquisitions is very much like a biodiversity inventory. The extended information handling requirements for addressing the issues of recollection and dereplication result in a fully-featured system. Furthermore, design and implementation of a natural products information system very nearly meets the requirements for supporting the government level decision making process; a system that would organize and represent existing natural resource data, assist in planning, and monitor harvest activities.

II. User Requirements

Computer software applications are first conceived through the definition of user requirements. The general requirements of a natural products information handling system are defined by the obvious needs for recollection and dereplication. To achieve a comprehensive solution, as described in the introduction, a system must offer key features that allow users to (a) link to commercially available data, (b) link digitally stored specimen photographs, (c) standardized data entry/capture protocols, and (d) offer extended spatial data manipulation capabilities using GIS functionality. Users need to both plan acquisition efforts and track organism collections.

A. Link to Commercially Available Data

Commercially available (non-proprietary) data on known natural products chemistry provides a valuable dereplication service for laboratory chemists that use biological activity directed isolation schemes. As an example, the largest natural products database, NAPRALERT (over 114,000 records), is a comprehensive source of terrestrial, marine and microorganism source chemistry literature. NAPRALERT is available on-line through STN International (Scientific and Technical Network) where it is linked to other chemistry databases' files by CAS Registry Number®) including CA, REGISTRY, BEILSTEIN, SPECINFO, MEDLINE, EMBASE, JICST and BIOSYS. The NAPRALERT database file can be searched by text/field including chemical class, chemical name, genus, species, and geographic term to name a few. Chemical substructure-based search capabilities are also available through STN and made easy with STN Express, a front-end software application. Chemical dereplication strategies and database resources have been recently reviewed.

It is important to provide structure to genus species lists that are obtained from outside sources where phylogeny, as reflected in taxonomy, is the first-choice method for grouping like organisms. Most existing databases include a genus species field but do not include Family and Order, and many do not even contain Phylum information. The utilization of these databases requires knowledge of taxonomy, genus synonyms, as well as all possible family/order classifications. As an example, a researcher working on a sponge of the genus Xestospongia would need to know that since 1977 this genus has been classified in four different ways: family Nepheliospongiidae, order Nepheliospongida; family Petrosiidae, order Haplosclerida; family Petrosiidae, order Petrosida; and family Nepheliospongiidae, order Haplosclerida. Using database technologies it is possible to incorporate multiple classification schemes such as those published for Xestospongia, arming a researcher with an in-depth knowledge of an organism without having to wait for consultation from an expert. With the power of a relational database design it is not only possible to include synonyms and common names, but also to apply multiple classification schemes such as chemotaxonomy, cladistics, or unresolved disputes over classification. This allows investigators flexibility when looking for trends within a complicated hierarchical structure.

To communicate with other databases it is possible to link on genus species name, CAS Registry Number, or the National Oceanographic Data Center (NODC) Taxonomic Code. Data format inconsistencies exist between systems and create problems for efficient data exchange, so an important application design consideration is to include standards that provide for data consistency within the system and for clean connection with major databases. For example, database linkage on genus species name is problematic because exact matches are required, any typographical error causes a matching error, and the data comparisons to determine a match are case sensitive. To address this issue, it is possible to use existing and standard datasets like the NODC Taxonomic Code. The NODC Taxonomic Code is a numbering system assigned to organisms, was entered and checked for errors, all entry is in upper case and is used by many database projects. In consideration for data exchange, standard data entry of organism marines can use the NODC-based dataset to present users with "menu pick" choices. While the NODC Taxonomic Code is primarily marine, it was recently extended to also contain some information on terrestrial organisms through U.S. Geological Survey collaboration; the dataset will be further expanded under the administration of the National Biological Service. A dataset like the NODC taxonomic code can be used to populate customized tables to effect data communication and support standardized data entry.

Another element of the known chemistry for a source organism is the geographic region where the tissue sample was collected. Many of the literature reports note the geographic region and some databases (including NAPRALERT) include a geographic term. For chemical dereplication it is sometimes useful to know where the collection was made and for expedition planning it is always important. It is possible to establish a separate link on geographic term and assign a latitude-longitude position for the record and addition to the GIS. For example, the term "Fiji" would be assigned the coordinate 17-30-00 south latitude—178-00-00 east longitude and placed on the map grid. While the exact position is not known it is still useful to collect this point within a polygon for a GIS-based query.

B. Link to Digitally-stored Specimen Photographs

Field identifications are an invaluable tool for dereplication by chemotaxonomy. The availability of easily accessible on-site photographs, organism descriptions, and distribution information is critical to field identifications. In some cases, identification down to only the family or order level can be helpful to a researcher. For example, a chemist working with a sponge that was identified in the field as belonging to the order Vergonida should expect to find bromotyrosine derivatives. In addition, acquisition programs of any scale face the issue of dereplication during expeditions when collections made early in the trip are confused with what is available for collection at the end. For example, when a Chief Taxonomist guides a marine organism collection expedition it typically requires that they make a reconnaissance dive to plan the specific collection effort. Both of these issues can be addressed by digital image capture in the field.

At the present time, the best methods used for photographic documentation of sample collections is to take two sets of photographs. The first set insures that you have an adequate image by using an E-6 process transparency film (Ektachrome), C41, or Polaroid film and develop it in the field. A second set is taken using true-color films (Kodachrome) which require photo-lab processing. Also, the inclusion of a color-bar or wedge in photographs is of considerable importance for true-color editing and the taxonomy or collection applications. Using advanced technologies to handle photographic images, existing photographic documentation can be used within the system, and future collections can be documented photographically with greater confidence in the field.

Using currently-available computer technologies, photographic images can be captured digitally in the field along with text information for the Specimen Data and Site Data records, and become immediately available to the database. Marine organism acquisition programs have user requirements that provide a good illustration of this functionality. For example, site specific collection planning can be enhanced by taking underwater video of the target collections, showing the footage to collectors, and giving them a plastic laminated print-out of the target organisms for use underwater. There is a growing application for video photography of underwater collections as cameras get smaller and resolution gets better. With video a collector can immediately see that an adequate image has been obtained for further use by taxonomists. For many of the same reasons as video, a rugged computerized still camera can be used by a plant collector in the forest; one drawback to computerized still cameras is that they require longer exposure times.

C. Standardized Data Entry

As discussed in the introduction, it is important to realize computer technologies so that natural products investigators find them useful. It is also important to extend this concept to include data capture, so that realistic searches can be performed on the dataset.

Collectors find it is very important to accurately document what an organism "looks like"—in many cases they first rely on the picture for recollection. Having a computer database that contains digitally stored photographs of an organism can be very useful in the field. In addition to the photograph, an organism's color is important and must be effectively communicated. Taxonomists find color to be very important in some cases. Color communication, however, can be very subjective. A variety of methods have been used to date, many result in color names like "rose" or "ocelot." Color swatch books used for past efforts mostly assign subjective names, and if these same books are used to match colors today there may be errors because the paper has degraded and the inks have faded—the colors may have changed. Careful color communication was used for the International Streptomyces Project where stable color crystals on microscope slide preparations were distributed amongst the participants. One effective and contemporary method is to use The Pantone Matching System®, an international graphic arts industry standard that contains around 1,000 color swatches. Pantone books are small, disposable, open like a fan, and easy to use in the field. The books are dated and it is recommended that they be replaced yearly to avoid color communication problems. Pantone colors are numbered, not named, and relational database technologies make it easy to assign color names to Pantone numbers. If only primary and secondary colors are used to standardize the entry, perhaps with two linked fields like red-brown, it becomes possible to perform realistic searches on this dataset.

Using graphical user interface (GUI) technologies, it is possible to provide users with intuitive "menu driven" navigation through the system, resulting in a heightened sense of orientation. Many non-graphical user interfaces to data are disorienting to the users. Menus and data entry forms (screen-forms) all have the same "look and feel" so the user knows what to expect; these same standards are applied to all elements of the system. Data capture is rapid, effective and relatively error-free. Text data are, in many cases, entered using "menu picks" from a "pull down" menu that contains default choices (like colors or taxonomic names)—there is no text entry into these fields, and no topographical errors. It is also possible to force entry in standard format, two examples are entry of date as month/day/year and entry of geographical position as degrees/minutes/seconds (and not degrees/minutes/tenths of minutes); these two features alone would solve the majority of problems encountered by the National Cancer Institute when they receive information from contract collectors.

D. Geographical Information System GIS

GIS is a full featured relational database that promises to be one of the largest computer technologies to emerge. GIS relates cartographic, or spatial data, with very large sets of related tabular information. What it does is integrate concepts of database management, computer graphics, and spatial modeling for managing geographic features. It enables the user to work interactively with, analyze, manipulate, and apply spatial data in computer graphic form called data layers. The coverage stores and displays cartographic data in the form of points, lines, and polygons. Points can represent the lat-long position of a collection site, lines can represent rivers, and polygons can represent areas that are the mapped boundaries of a water mass, forest type, or other natural features. Related to any point, line, or polygon feature are attributes in a relational database manager. Attribute information is thematic or reference data and can be collection site physical characteristics, flow of a river, or the range of an organism's occurrence. The simple structure of map data layers related to data files offers great capabilities for the entry, manipulation, query, and display of large sets of spatial data. While the structure is simple, the power is exponential. Large sets of continuous spatial data can be accessed for analyses between and among layers that allow complex analytical functions to be performed on the database. For GIS technology reviews see.

GIS is the acronym first assigned to the term "graphical information system" and has since changed to mean "geographic information system". GIS is a method for extending traditional database queries to include a spatial element. GIS project hierarchy typically follows:

Project

Index

Category (index level)

Map

Feature

Attribute

Figure 1B:
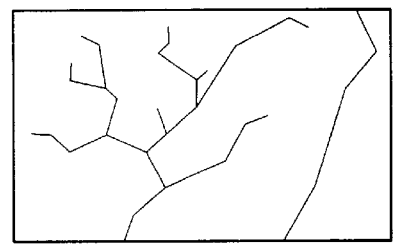
Figure 1C:
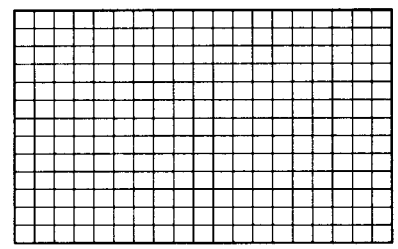
Figure 2:
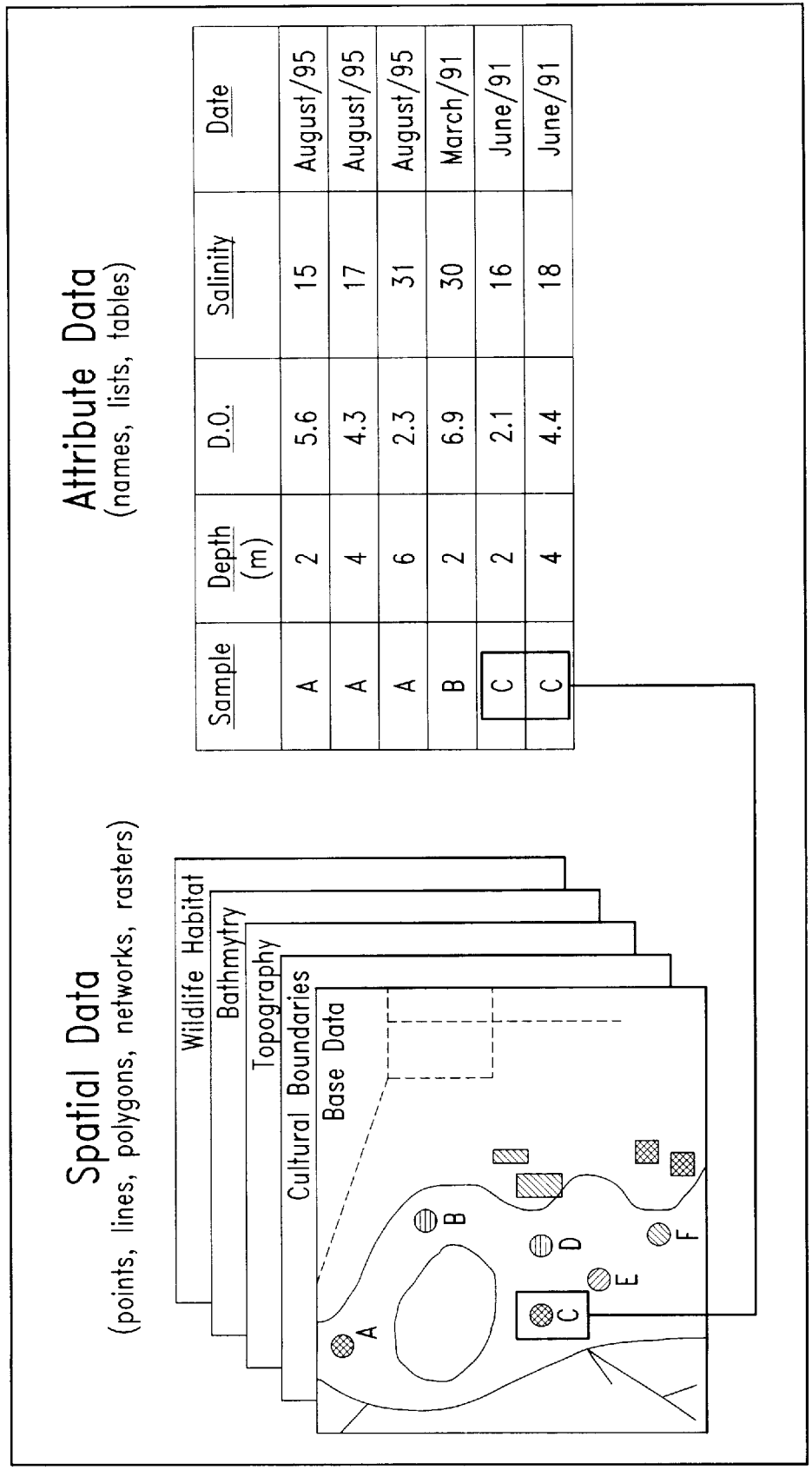
FIG. 2 is a correlation of spatial and attribute data.

Referring to FIGS. 1 and 2, "Features" in a GIS are spatial data including points, lines or polygons that are assigned "Attributes" and represented spatially on a map grid. As an example, in a natural products-related GIS there are 'point' "Features" for collection sites that are assigned the "Attribute" of a corresponding traditional database text-field table that contains information on the site; this table is joined to a second text-field table that contains information on the specimen. In addition, there are 'polygon' "Features" that are assigned "Attributes" for salinity, temperature, or substrate-type. There may be lines included to represent a marine shoreline but they do not necessarily require "Attribute" assignments. In other GIS projects 'lines' could represent "Features" of river centerline or city street networks.

For example, GIS allows for query the traditional text-field database tables for:

sponges, collected during August 1995, red in color, and to extend the query in the GIS to include:

salinity value.

Salinity value does not exist as a text-field in the traditional database table. This GIS spatial analysis query collected only the red sponges from August 1995 where the 'point' (collection site) fell within the appropriate 'polygon' (salinity value). The power of GIS is realized when spatial data are added at a later time. For example, an updated salinity map, or a chlorophyll map acquired using satellite-based remote sensing technologies. Any spatial data can be added to the GIS and used selectively.

Alternatively, in a zoogeography-related GIS, the 'polygon' "Feature" could be assigned the "Attribute" of a sponge species to represent range of species occurrence. Several 'polygons' can then be layered (like sandwiching species-occurrence maps from the upper corner of bird book pages). This allows users to pick a point on the map, say Fiji and query the GIS for a species list that is specific to that region (a list of all polygons that the point falls within). The range of species occurrence 'polygons' can be updated to include new zoogeographic data for a particular species.

GIS analysis falls into two basic categories: spatial analysis and grid analysis. Simply stated, spatial analysis is the determination of points within or outside of polygons (FIG. 1A), overlapping polygons, and intersecting lines (FIG. 1B), to mention a few. Grid analysis makes us of raster (or pixel) data, each uniformly placed grid square is the same size but has a unique position with an assigned value. As spatial entities, the grid squares shown in FIG. 1C are related by their exact positions and also by their relationships to other spatial features.

Natural products acquisition programs have intensive requirements for both mapped and tabular data. It is important, however, to provide GIS technology to natural products investigators and biodiversity inventory projects on a specific and appropriate level. Scientists are sometimes frustrated by full-featured GIS products that require years to become proficient at. Information handling system design considerations should include a custom interface that gives natural products investigators selective access to high-end GIS.

Global positioning system (GPS) technology is commonly available, especially for marine navigation, but is now beginning to appear as a part of many other practical applications. For example, the freight trucking industry uses GPS to track the position of their individual trucks on a nationwide scale and car rental companies are advertising GPS controlled route tracking through a map interface in each car. GPS technology delivers as advertised—it is a system that provides a geographic position on a global scale. GPS technology is based upon transmissions from a fleet of 28 satellites. Their orbits are synchronized so that transmissions from at least three different satellites can be received at any position on the earth at any time. Based upon these transmissions, a GPS receiver calculates a position (usually latitude–longitude), and on the quality of the signal coupled with strength of geometric figure of the constellation of satellites overhead. With a clear signal it is possible to achieve positional accuracies of +/–10 m (95% confidence interval) using a single unit in autonomous mode; the signals do not penetrate obstructions like trees or buildings. These accuracies are not typical, however, because the military dithers the signals with selective availability (SA) to render it useless for missile guidance systems. Typical accuracy is +/–100 m for autonomous operation, but real-time (without post-processing) sub-5 meter and sub-meter accuracies are possible using differential methods. One drawback of high-accuracy differential GPS is the time required to return the position, calculations can take up to 5 minutes as compared to near-instantaneous for lower accuracy methods. GPS data are point data, and in some applications GPS points are acquired continuously to create lines. GPS points provide the positional control for spatial data sets of any size and are a fundamental element of most GIS datasets.

Figure 3A:
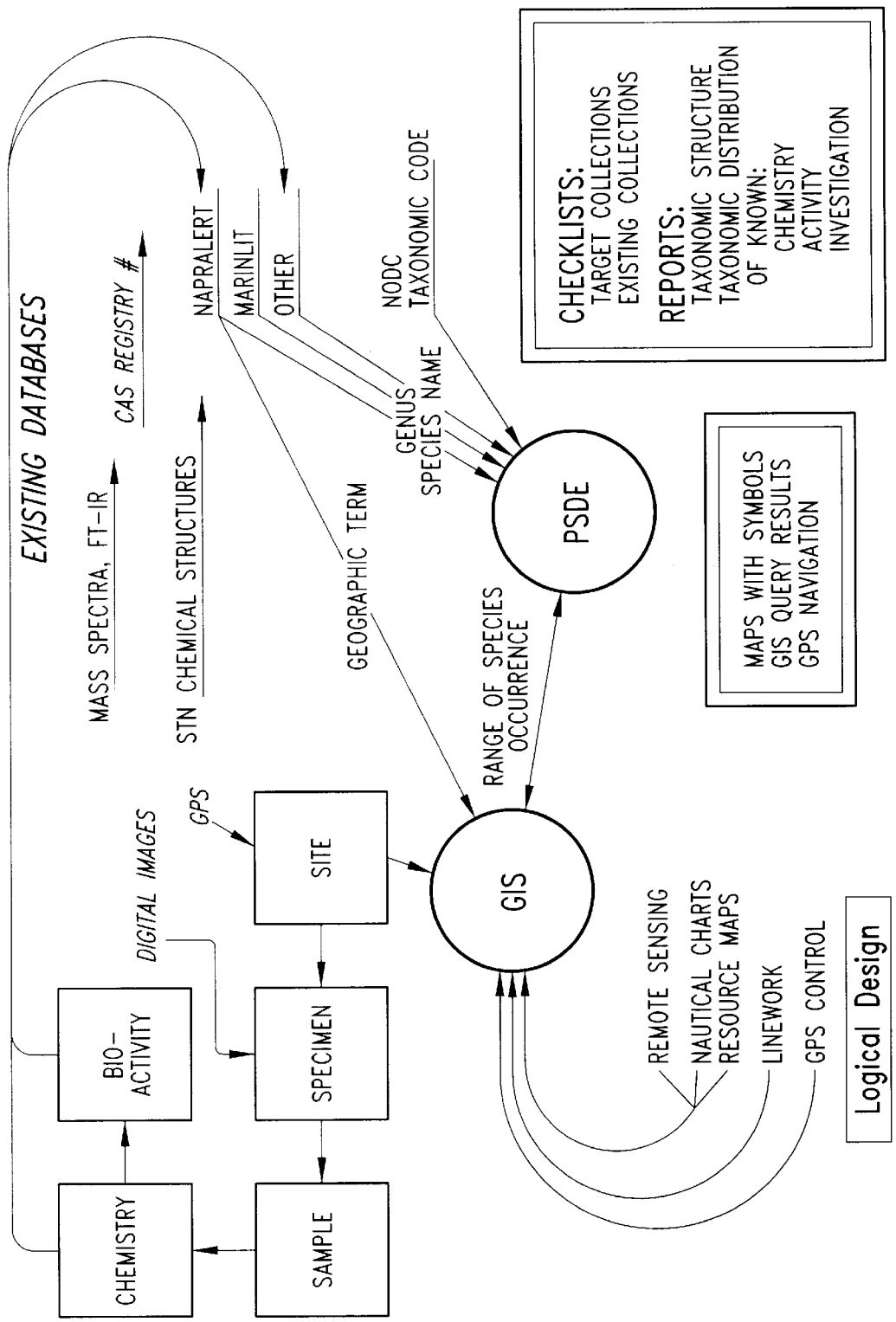
FIGS. 3A–B are logical design diagrams illustrating the relationship of data sources to the present invention.
Figure 3B:
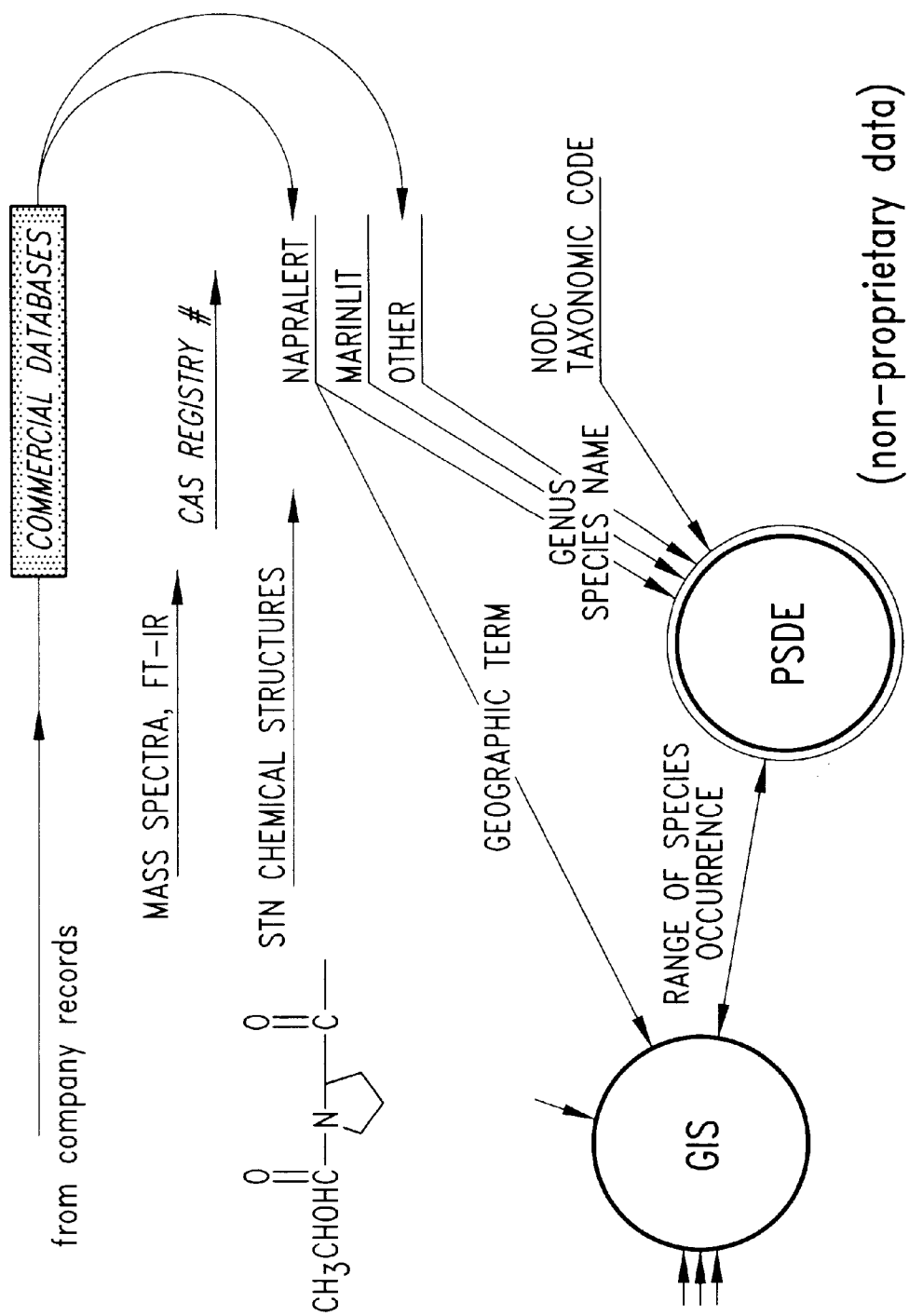

One of the most powerful features of a comprehensive information management system that supports natural products acquisition programs is use of spatial data and GIS technology. GIS technology allows the system to step beyond the requirements for a normalized data model in a relational database design. GIS allows for addition of those data, which have a spatial element, as an overlay. Importantly, spatial data can be selectively added on a need to know basis, and, most importantly, addition of these varied data does not affect the logical design and data model, which is shown in FIGS. 3A and 3B.

E. Expedition Planning

The best supporting information on the environment is mapped. Most biological resource studies are carried out at sampling stations with known positions (latitude and longitude), and a significant amount of these existing data can be assembled for project support in some cases. If these data are not summarized in mapped format, they can easily be plotted onto a base map. The most useful base maps for planning marine-based collecting expeditions are nautical charts, because navigation is required to implement the recollection efforts. Using maps reveals spatial relationships in ways that are not possible with data in tabular or other format. Information on the species' habitat, including temperature, substrate, orientation and available light, can be compiled with information on the species' overall distribution and abundance to identify specific sites where the organism is most likely to be found. A priority ranking can be assigned to target desirable sites and effectively direct the field efforts.

Additional mapped information can be obtained. Maps and nautical charts were historically constructed from survey measurements or from aerial photographs but are now being upgraded by satellite-based remote sensing technologies (aircraft-based in some high resolution applications): it is not uncommon to find some mapped features misplaced by a kilometer. There are repositories of satellite image data and access to them is possible in many cases, however, the data resolution or data type may not be suitable for the specific recollection effort. New technologies for spatial data acquisition make it possible initiate a mapping effort and define specific land or resource features. A review of these technologies, collectively referred to as Remote Sensing, is beyond the scope of this chapter; refer to the reviews by Lillesand & Kiefer and Richards for additional information.

In addition to using remotely sensed data as a GIS 'backdrop' and map, it is possible to create GIS "Features" from these data for use in spatial queries. At the present time, multi-channel spectral-scanning (MSS) technology is widely used because it can acquire data on multiple discrete (preset) bands, making it possible to segregate land or resource features by their reflectance and assign primary or secondary block colors. There are many different methods for acquiring these data, and many different data formats. In forestry applications, tree species with different reflectance values (spectral signatures) can be segregated from within a forest stand: coniferous trees can be assigned a yellow color block, and deciduous trees can be assigned blue. In marine applications MSS is particularly useful because it can detect submarine resources (to a depth of 20 m depending on water clarity) and segregate coral reefs from other substrate types. Perimeter boundaries can be defined for these color blocks, or the color value of individual raster pixels can be used to define GIS "Features." For a recollection effort that targets specific organisms, mapped MSS or other data (e.g., aerial photographs) are planning tools that easily supplant other resource specific information.

In any remote sensing project there is a tradeoff between the spatial vs. spectral data quality. For example, a 7-band MSS Landsat Thematic Mapping (™) scene covers an area of 185 km2 and has a file size of approximately 235 megabytes. The Landsat TM data have a pixel resolution of 30 m, and are generally not considered useful for applications other than large scale resource inventory. SPOT data, MSS data acquired by a French satellite, offers higher resolution: 20 m pixels for color, and 10 m pixels for panchromatic (black and white) data, and allow visualization of buildings and roads; however, to cover an area equivalent to Landsat TM requires 9 SPOT scenes with a corresponding file size of 2.1 gigabytes. Aircraft-based MSS are commonly used for higher resolution applications. It is possible to provide coverage at common mapping scales used by the U.S. Geodetic Survey for 15 minute quadrangles (=1:60,000) and 7½ minute quadrangles (=1:24,000) with a pixel resolution of approximately 2 m. Coverage of aircraft-based MSS is commonly limited to (no greater than) the 1:60,000 scale. Use of remote sensed data requires a powerful computer for image display and processing; however, these data can be resampled to yield smaller file sizes for use on computers with limited capability.

III. Implementation of a First Embodiment

A. Standardized Entry Protocol Modeled after the Current NCI Format.

Summary—The NCI Marine Site Data, Marine Specimen Data and Terrestrial Plant Data forms were re-created using a graphical-user-interface development tool (Paradox for Windows V. 4.51). Entry choices on NAPIS forms are standardized and in some cases forced for compliance (e.g. date, latitude-longitude). Developing a prototype Terrestrial Plant Data form was added to this specific aim.

Objective—To standardize the entry protocol and provide data consistency, easy data entry, and record management.

NCI Modeled—Standardized entry protocols allow for data consistency. A utility choice for "Save NCI Report" generates an output that is specific for importation into the NCI DIS. Each form contains the following standard fields:

Log-on procedures. Users enter their name each time they log into the system. User names are automatically added to each form in fields denoting entered by, last modified by and completed by.

Site and/or Sample numbers. The NAPIS numbering convention is a composite number including a project prefix, year, month, day, site, and sample. The number can be extended to include an extract and fraction suffix. For example:
W1 99408020101FA01
The number is automatically generated and presented in a dialog box to the user when entering into a Site or Specimen form, the number is modifiable in the dialog box but is automatically entered into a restricted field in the forms. The NCI number generator is also included.

Form Logicals. A yes/no box is checked for "is form complete?" This allows review for completeness.

Marine Site Data. This form appears on the computer screen in similar format to the form published by Pomponi, 1988. Standardized entry was developed for the following fields:

Latitude-Longitude. Entry is forced to require degrees-minutes-seconds as opposed to degrees-minutes-tenth of minutes. Users are also presented with pull-down menu choices for entering a datum, WGS84 is the default (World Geographic System 1984).

Habitat. Users are presented with a dialog box where default choices modeled after the "Marine and Estuarine Habitat Classification System for Washington State" (Dethier, 1990) for five categories including: systems, subsystems, classes of substrata, energy, and modifiers. For example: Marine, Subtidal, Rock: Low Energy, Shallow.

Marine Specimen Data—This form appears on the computer screen in similar format to the form published by Pomponi, 1988. Standardized entry was developed for the following fields:

Taxonomy. Users are presented with menu driven hierarchical "entry pick" choices for data field entries. The tables that populate the menu choices are from the PSDE "standard checklist." For example, when the Kingdom Animalia is selected only the animal phyla are presented to the user for choices; when the Phylum Porifera is selected only the sponge classes are presented to the user for choices; this steps down to the species level where the species-variant-authority choices for a specific Genus are presented as choices.

Internal and External Color. The Pantone(R) Color system is adopted as a color communication standard. Easy to use, and commonly available, color swatch (978 colors) books allow for accurate documentation of the organism's color in the field. Pantone colors are numbered and these numbers are assigned a three-category description by NAPIS. The color description categories are based on appearance, color and hue and are presented to the user within a dialog box. Appearance choices are after NCI data choices, and color and hue are based on primary and secondary color choices. For example, Pantone #310 is described by NAPIS as light, blue, green. Pantone colors were described by a artist/color expert for NAPIS and associated to the Pantone numbers. Colors may also be entered without using the Pantone system.

Morphology. When Porifera is entered into the phylum field the user is presented with a default set of "look up" choices for entry into the morphology field: branched, vase, tubes, etc. (NCI morphotypes), the default set of choices is customizable. The advantage of this standardized entry protocol is in the consistency—it allows for completeness in database searches by eliminating the variability seen with different entry styles.

Habitat. Is assigned a default value based on the Site Data entry and is modifiable. Abundance, Organism Parts, Mucus, Odor, Epibiont Cover, Cyannobacteria, Zooxanthellae, Zooanthidea, Relaxation, Fixation, Preservation. All have defined pull-down menu associations to look-up tables for default choices.

Terrestrial Plant Data—This form appears on the computer screen in similar format to the dBase III Clipperized run-time version distributed to collectors by the NCI. Standardized entry fields are as noted for both the Marine Site Data and Marine Organism Data forms.

Conclusions—The graphical-user-interface and hierarchical "menu pick" entry methods provide data consistency, reduce the amount of time required to enter data and reduce typographical errors; these features are especially useful in large-scale programs where large amounts of data are captured and handled. Chronologically-based numbering convention and form logicals are efficient methods for record management.

B. System Requirements

System Requirements

Hardware Environment
Processor: 486 or greater
Memory: 32 MB minimum, 64 MB recommended
Disk Space: 275 MB required (not including OS and supporting software), 1 GB recommended (for GIS)
Virtual Memory (95): Windows Manage—50 MB minimum
Page File (NT): 100 MB
Release Media: CD-ROM
Software Environment
  Windows 95
  Windows NT 4.0 (optional)
Supporting Software Requirements

Desktop Database
  Paradox v 7.0   (requires additional 25 MB disk)
Customer Report Generator
  Crystal Reports v   (optional—requires additional 8 MB disk)
Chemical Compound Data and Structure Handling
  ISIS/Base and ISIS/Draw v 2.1 (optional—requires additonal 25 MB disk)
Desktop GIS
  ArcView v 3.0, with Spatial Analysis (optional—requires additional 65 MB disk)
Personnel Requirements

Beta Test Site Manager
  responsible for communication with WPBM on bug reports and feature enhancement requests
Beta Test Participants
  responsible for using NAPIS, testing the workflow in assigned modules, and creating bug reports for communication to WPBM
Database Administration (optional)
  responsible for migration of legacy datasets into NAPIS tables Operating System software industry trends favored the Windows NT platform. Windows 3.1 (running on DOS) would be replaced by Windows 4.0 (Chicago) that was purported to be a non-network server version of Windows NT with 32-bit processing capability and DOS was to be discontinued in Q1 1995. NAPIS can be modified for Windows NT.

Software Versions for Windows 3.1 can be upgraded to NT. Programming for seamless application interface may become obsolete and impede functional development. For example, programming Paradox to emulate Object Link and Embed (OLE) to the image editor Adobe Photoshop.

For application development, Paradox v.4.5 (upgrade from 4.1 released for Windows in Q1 1993) was available with the capability for SQL interface with Sybase SQL Server and can run (slower) on NT. The NAPIS user interface prototype was developed using Paradox with an eye toward version upgrades with the required OLE compatibility with image editing software Adobe Photoshop v. 2.5 (Windows version released January 1994). Photoshop 3.0 is now available for NT (September 1994) and does not support OLE-2 but does support image capture add-on's (e.g. scanners). However, the new Intergraph DBAccess development tool solves the interface problems with image handling and is consistent with the NAPIS development plan. Experimentation results show that DBAccess is favored for NAPIS over Paradox because of its existing capability to network and seamlessly interface with other Intergraph modules, especially with respect to image handling.

For GIS, AutoCAD v.12 was released in January 1994 and ArcCAD was released in February, however, CadOverlay was only available for DOS with no planned upgrade to Windows and raster image overlay capability was critical to the data acquisition. ArcCAD software development was planned to be rolled into ArcView but we did not want to develop our application using software that was planned for obsoletion. An alternative GIS software Intergraph has the required capabilities, and it was available for Windows. Intergraph is also useful because of extended capabilities and strength of the company position in the marketplace. Intergraph development trends included migration of their UNIX-based GIS modules to the NT platform (for release in June 1994, NAPIS was upgraded) which provides extended Workstation capabilities including relational Sybase SQL Server and system security and is consistent with NAPIS development trends. In contrast, other GIS software functionality is migrating slowly and tentatively from DOS to Windows 3.1.

Hardware Requirements for image acquisition may require configuring a second computer. For image editing, a specific video card and monitor may be required to achieve true color results based on the Pantone (R) Color communication standard. Also, image capture from video tape may require a different, but specific, video graphics card. Use of a second computer solves an IRQ addressing problem that was faced on the primary computer. Ideally, the two computers should not be networked.

Prior experimentation not only successfully developed all functional elements of the original design, but also provides the sound basis for technical development of alternative embodiments of the NAPIS product.

Objective—To develop a prototype system and perform an example demonstration which includes: Use of existing data to populate the GIS and enter into the Marine Site and Marine Organism Specimen forms.

An example search that includes:
  conventional database
    all marine sponges from the study region, and
    "branched" morphology (NCI morphotype), and
    red in color, and
    collected during march and april, and geographical information system (GIS)
  associated with eelgrass meadows Database Description—The Paradox-based user interface prototype was developed using the Paradox database table structure. All forms tables were created with simple data types allowing for easy translation with Sybase or other database format (e.g. ORACLE NCI, DIS). The Paradox tables were subsequently exported to Sybase SQLServer via Paradox ODAPI engine and Borland SQL-Link for Sybase. This implementation populates GIS tables where the only table modification is addition of two standard maplink fields to the Site Table. Paradox can read-write Sybase tables directly through programmed TCursor assignment via this described SQL-Link. Look-up tables for standardizing entry with hierarchal menu-pick choices remain as part of the user interface. For NAPIS portable field use without native GIS, Paradox writes to Paradox tables which are later exported to Sybase. PSDE tables containing taxonomy data are native on the Paradox user interface.

Software—The software packages were assembled on both the Windows 3.1 and Windows NT 3.1 operating systems. Implementation of the total system requires exiting the applications to enter others, however, many features can be implemented using advanced Dynamic Data Exchange (DDE) technologies including Object Link and Embed (OLE). Query of the Sybase database tables is possible using Paradox initiated SQL Link to the Sybase Server. To determine an appropriate computer operating system for integration of the required software packages while considering the timing of software version release and rapid pace of software development required extra review and evaluation, the following software packages were used-Paradox for Windows V. 4.51 and Adobe Photoshop for Windows V. 2.5

GIS software proposed but eliminated from consideration because of limited raster image handling capabilities developed by a third-party vendor include—

ArcCAD for Windows, AutoCAD for Windows, CAD Overlay (not available for Windows) GIS software (subsequently identified as appropriate and included) Intergraph: MGE Basic Nucleus, MGE Basic Administrator, MGE Base Mapper, MGE Projection Manager, MGE Analyst, MGE Grid Analyst, MGE Map Finisher, MGE Terrain Modeler, MGE ASCII Loader, IRAS/C, Microstation 5.0 Sybase SQL Server 10-full development version (added for interface with GIS)

Hardware—Development of the system required two computers because of graphics driver requirements. The video-frame-grab technology required specific graphics drivers that were not compatible with the other precise image editing system graphics drivers. However, only one system is required to actually run NAPIS. The following systems and peripherals were assembled to develop the prototype:

Image capture system—486-DX2-33, 8 mb RAM, 250 Mb IDE HD, Matrox Video Graphics Board (Svideo frame grab), Nikon Cool Scan (slide scanner).

Database, GIS and image editing system—486-DX2-66, 32 Mb RAM, 1.2 Gb SCSI HD, CD-ROM, ATI graphics card, NEC SFGp Monitor, Shinko S446i dye-sublimation full-color printer.

Implementation—The below listed and italicized titles are menu choices from the NAPIS main menu screen. Paradox for Windows v.4.51 will also run under Windows NT v.3.1.

PSDE—The PSDE (phylogenetic structure database engine) is the taxonomic "standard checklist" based on the NODC Taxonomic Code, and provides the interface to commercially available databases by linkage on genus species names. The menu-driven selections are:

Create Custom Checklist—Not implemented, table structures investigated, described in the Phase II Proposal.

Collection Set Data—As described above the log-in protocol to the Collection Set Data automatically tracks modifications to a record by user name. The menu-driven selections are:

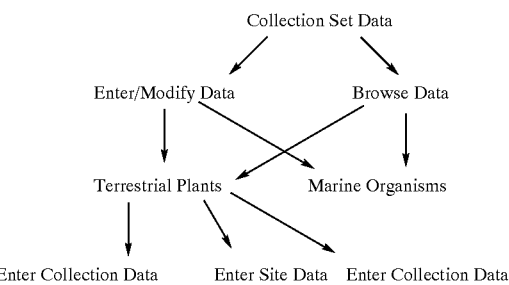

Screen-Forms—are described above and examples are illustrated below.

Image Handling—The following elements of image handling were addressed:

Image capture is not implemented from within the NAPIS prototype application, it is handled from a separate computer because of video-graphics requirements. Images are captured digitally using two methods including slide scanning and video-frame-grab, files are transferred and related by file name to a graphics field in the NAPIS prototype.

Image Link to screen-forms of low resolution thumbprint images are linked by DDE to the graphics field in an individual record using Microsoft Paintbrush as the OLE-I application in a *.bmp file format. This allows a color image of the specimen to be viewed on the screen-form for a given record. File size of images stored using this format are roughly 80 kilobytes. Seamless interface with Adobe Photoshop is not possible using OLE-I.

| PSDE | | |
|---|---|---|
| Standard Checklist | Alternative Checklist | Create Custom Checklist* |
| Taxonomy  Bioactivity/ Chemistry | Alternatives One, Two, Three Sponges-Bergquist Sponges-vanSoest Sponges-Hooper | |

Taxonomy—This screen-form table structure consists of seven tables that have a key index and secondary index on the NODC taxonomic code fields that link the tables in a hierarchy; three additional tables that contain information on synonyms and common names are linked by a key index to corresponding NODC taxonomic code and code suffixes. Taxonomic levels included are: Kingdom. Phylum, Class subclass, Order suborder, Family, genus species variant authority.

Bioactivity/Chemistry—The Taxonomy table structure is reproduced for this screen-form, without links to synonyms and common names, and is linked to two tables containing chemistry and biological activity data (obtained from other databases) by a combined secondary index on the two fields containing genus species names. The CAS registry number is the key index in the chemistry table and links to the CAS registry number plus suffix combined key index in the bioactivity table.

Image Editing and Printout of high resolution specimen image is stored in a separate *jpg file format and can be viewed from the image-editing software Adobe Photoshop. Adobe Photoshop does not support OLE in the current version and this application must be worked with independently. The image editing computer system was configured with an ATI graphics card to specifically drive a NEC Multisync Sfgp monitor that supports the Pantone (R) Color standard. This configuration allows images to be edited on-screen to match Pantone colors. During editing the user can hold the Pantone color swatch up to the screen and adjust the screen color to match.

Photoshop produces an output file (to the printer, Shinko CHC-S446i for Phase I) that produces a photo-real printout that can be used with the Pantone color swatch book in the field to confirm specimen color. File sizes for 4"×5" truecolor photo-real computer printouts are roughly 4.3 megabytes before compression and 503 kilobytes after JPEG lossy compression. Storage of 100 high-resolution images requires roughly 50 megabytes of storage and is considered reasonable.

GIS—Working with the GIS application requires exit from the NAPIS prototype and startup of the Intergraph suite of modules. Sybase SQL Sever is the associated database. A thorough investigation of existing information in the form of spatial data was made for San Juan County, Wash. A grid was established using the North American Datum from 1927 (NAD27), linework for the shoreline was imported and raster images were overlaid, scaled, transformed, rotated and deformed (warped) to the coordinate base. Quality of available existing data were compared by review of edge-matching. The following existing data were identified and used in the Phase I Study:

Shoreline information in vectorized form was obtained from the San Juan County Assessor's Office along with United States Coast and Geodetic Survey Triangulation Station positions on NAD27. These data were provided in DXF file translation format and imported into the GIS, and were used to establish the coordinate and map projection base. These data were considered to be best because of the standard methods used for digital capture within the Assessor's Office and the NAD27 based construction of data.

NOAA Nautical Charts were obtained in raster format from Resolution Mapping, Inc., (Newcastle, Me.). One color chart is roughly 10 megabytes in size and are delivered in 3"×4" tile files.

Resource information on eelgrass and kelp was scanned at the local intergraph office and imported in raster format from the Coastal Zone Atlas (Hallauer, W. 1978. "Coastal Zone Atlas of Washington" volume 3. State of Washington, Department of Ecology).

Resource Information on eelgrass and kelp was obtained in digital form as an ASCII download from ArcINFO at the Washington State Department of Natural Resources based upon the Coastal Zone Atlas and other information internal sources.

Aerial photographs used in photogrammetry were obtained from the Washington State Department of Natural Resources and scanned in black and white for importation as raster images.

Queries—Customized query dialog box, no standard queries are included.

Reports—Standard report types included are:
PSDE Checklist including chemistry, bioactivity, synonyms, common names and higher taxonomy by genus species name, and Site Summary:
Site record with Collection records
Single Site
Single Marine Organism Collection record
Single Terrestrial Plant Collection Record Maintenance—This typical database feature is designed to include:
Access for look-up and other table modification
Backup
System Passwords Conclusions—These substantive conclusions are offered: Implementation. While Paradox for Windows V.4.51 was appropriate for developing a prototype and has the capability to query the Windows NT based GIS-Sybase server database tables via an SQL link, the system should be developed with a more powerful development tool and dbaccess by Intergraph (Windows NT version due for release Q4 1994) is recommended. Intergraph is Windows NT (network supporting) based and offers an appropriate suite of software, hardware and service products for high-end application development, and, notably, third-party vendors are not required when using Intergraph technologies. Windows NT ideally should be used as the operating system for future development of NAPIS.

Image handling. Video-frame-grab is a rapid method for image acquisition and well suited for field application, however, the resolution is low for critical follow-up studies. Higher resolution photographs should be acquired in addition to video. However, field video recording of specimen collections insures that an image is indeed acquired and is preferable to the alternative method of duplicate Ektachrome still photos (where color quality is uncertain) and on-site E6 film processing. Intergraph products have the capability to show a low resolution image within a screen-form without having to create a second lower resolution file; Paradox requires both file formats.

GIS. Using existing information requires accurate information on the goodness of how those data were generated; a new term, metadata, has been coined in the database community to identify this issue. Data acquisition technology has advanced at such a rapid pace that older spatial data are often obsolete; for example, GPS control for rectification of aircraft-based multi-channel spectral-scan digital image capture allows for relatively high accuracy current information on resources with the added capability for image analysis. Using advanced technologies is appropriate for application in large-scale natural products acquisition programs. Advanced technologies allow for the requirements of dereplication, recollection and expedition planning to be used as assets that enhance the probability of success for drug-discovery efforts.

IV. Implementation of a Second Embodiment

A. NAPIS Development Design

NAPIS development follows a simple body of methods, rules and procedures that are used to ensure that tasks are carried out in an efficient and logical manner. The development plan allows for an orderly progression from requirements to implementation. To ensure continual progress, each stage of the process is results-oriented and is measured by the completion of a specific deliverable as a milestone. This plan prescribes a structured approach to managing the system development process and tracks critical activities allowing the development team flexibility to determine the most effective ways to fulfill the system requirements.

B. Requirements Analysis

This embodies the results and conclusions of the first embodiment, described above, and they are listed here for reference:
Dereplication
Recollection
Expedition Planning
Interfacing with Chemistry and Other Databases
Standardized Entry Protocol Modeled after the NCI
Prototype Development
Existing Database Review The second embodiment updates, amplifies and extends the first embodiment with these additional Specific Aims. The Specific Aims define the requirements for development of NAPIS Dissemination of Information
Standardized Data Capture and Exchange Methods
Amplified Phylogenetic Structure Database Engine (PSDE)
Extended Advanced Technologies Pilot Study
Biodiversity Inventory Project Support To serve natural products chemists and drug discovery efforts worldwide the system will be extended from containing information marine organisms to also include terrestrial plants and microbial organisms Access to the technology (specifically, costs) is considered and addressed by offering different levels of feature capability To accomplish this objective the system has three distinct components, each component is designed to function independently and to interface with each other NAPIS Core Providing direct on-line Internet access and client-server support, the core system is the fully-featured program application and information repository, and is the stage for information exchange.

NAPIS Laboratory A laboratory management tool that tracks development from sample acquisition and handling through chemistry and biological activity testing. This system can be configured to provide core-level network support features at the laboratory level. Includes GIS-mapping capabilities.

NAPES Remote A tool for portable field-use by source organism collectors. Tracks specimen/sample collections and their handling. Maps collection sites with limited GIS capabilities.

In practice, investigators that have limited requirements can interface with the NAPIS Core via an Internet node without owning a NAPIS module by using the World-Wide-Web (WWW) technology via Mosaic. Independent collectors who provide source organism tissue samples for drug development or provide biodiversity inventory services can run NAPIS Remote and interface with NAPIS Core to address their dereplication and expedition planning needs. Investigators at the project management level can run NAPIS Laboratory configured to have all the features of the core system, provide network support to their collectors running NAPIS Remote, and only interface with NAPIS Core for access to the extended information repository.

Functional Requirements

Network and Internet Connectivity functional requirements of NAPIS restrict the system to a client-server environment for efficient graphical display.

Independent users that use Mosaic interface to the system (without a NAPIS module) require a greater number of core system resources and limited capability. Mosaic and other WWW clients can browse servers and view WWW documents. However, they can only do so in a limited fashion. That is, the client can display text, graphics, and even accept various forms of input (e.g., clickable regions, entry forms, edit fields, etc.). These input mechanisms will be translated into meaningful SQL queries so that the Intergraph software can accept it. Then, the Intergraph software will send out results that in turn get transmitted back as an HTML document (Hyper Text Markup Language), which is the type of document that all WWW clients (e.g., Mosaic) can display.

In the TCP/IP client-server environment (using a NAPIS Laboratory or NAPIS Remote module), clients will directly interact with the server; the NAPIS module essentially distributes the resource allocation load to the client system for video map display and assembly of structured query language (SQL) queries, leaving the core system free to handle raw queries of the core tables. Intergraph software design is client-server based and is well suited to support the image and GIS intensive NAPIS application. Intergraph software is implemented in the Windows NT based graphical user environment, allowing users to log into the system running the Intergraph GIS and tell it to display at their system; the resource allocation is distributed between the client and the server systems.

IP is a practical method of transmitting data from one location to another. What makes it so appealing is its scalability. No other protocol can come close to the number of hosts that an IP network can handle (without becoming a victim of their sizes—translating into bad performance). The beauty of using IP is that private IP networks can be built and maintained in parallel with the networks associated with the Internet, this provides maximum levels of security. For example, where a large government or private organization requires installation of a mission-specific NAPIS system (a secure on-site NAPIS Core supporting the other modules) using the same protocol that the Internet uses, segments of the private network can be linked to the actual Internet for gateways or for specific clients. These controlled points are typically called firewalls. In addition, private networks mean that 100% of the bandwith is used for its intended use. None of the bandwidth is shared or even publicly available to the Internet and its associated population.

The best communications option is a T3 connection, where the bandwidth available is 45 Megabit. This is 4.5 times faster than the output of standard Ethernet, which operates at a 10 megabit transfer rate. The NAPIS server will be operating over Ethernet which means that there is more bandwidth across the T3 than the NAPIS server would be able to put out. However, multiple NAPIS servers on different Ethernet segments would be able to utilize the bandwidth (4.5 servers). The NAPIS server would ideally be the sole machine on an Ethernet segment, thus giving it complete control of the 10 megabit bandwidth (with the exception of the router than would transfer the data to/from the Internet). The next step down would be T1, which operates at 1.54 megabit. This is a common connectivity point for many universities and large corporations. Further is fractional T1 in 56K increments going down to 56 kilobit. Anything smaller is breaching modem speeds, which is far too slow for this application.

There is an additional way to utilize 45 megabit bandwidth of a T3, and that is to implement the NAPIS server on an FDDI or other 100 Megabit backbone. This would have to be directly routed to a T3 backbone in order to make the most use of the T3's bandwidth. 100 Megabit Ethernet requires separate hardware and software (drivers) for the OS and are typically much more expensive than standard ethernet hardware (and software).

Database Design specifications are based on the database interface and data transfer requirements. The NAPIS database should be constructed on Microsoft SQL Server for Windows NT. Databases are joined by an index on genus species names, Chemical Registry Number (CAS#) or geographic term. Digitally stored images are linked to the Specimen, Chemistry and Bioactivity Data records by discrete file name. The Site Data records contain two fields that link to features in the GIS. Other GIS features corresponding to natural resources are only linked graphically within the GIS. Investigators running the supporting NAPIS modules will create a database of locally searched first downloaded images and map data, updated as required. Larger organizations with configured local or wide area network systems will also download large datasets from NAPIS Core to populate and update their systems. Database design specifications are related to resource allocation as generally noted above. Specific physical design elements will be defined in the Preliminary Detailed Analysis and Detailed Analysis with the Intergraph and Microsoft corporation contractors.

Extracts of the NAPRALERT database are directly incorporated into NAPIS. These region-specific datasets will be configured by NAPRALERT for transfer to our system according to our specifications for fields delimiters and other requirements.

Standardized Data Capture methods applied by NAPIS generally rely on capabilities of "graphical" interface software technology. The graphical interface serves to: eliminate text entry errors, standardize entry choices and increase the speed of entry. Traditional text-field data entry can be standardized using "pull down" menus that present users with a set of default "menu pick" entry choices; a subset of entry choices can also be presented as default through use of hierarchical links. Customizing the interface using radio-buttons (pick only one choice) and checkboxes (pick more than one choice) are other efficient entry methods. Dialog boxes can be called and overlaid on the screen-form when entry choices exceed space limitations. Using graphical interface technology, a standard work-flow can be established that directs users from the system level to the screen-form level. These methods standardize entry and provide users with a heightened sense of orientation to the system.

Data entry forms (screen-forms) allow for linkage to be established between database tables, other forms, and files (e.g., digital images) that relate to input of information on a single sample. The forms provide an opaque interface between the user and the complex database system. Graphical interface methods are used to navigate through the system. The NAPIS forms, designed to track sample acquisition and development, are listed and described here:

Marine Organism Site Data. Is designed for data on collection sites where many marine organism specimen/samples are collected.

Marine Organism Specimen Data. Is designed for data on marine organism sample voucher specimens.

Terrestrial Plant Specimen Data. Is designed for data on terrestrial plant sample voucher specimens, includes site data.

Microorganism Specimen Data. Reflects the Terrestrial Plant Specimen Data form with obvious modifications for documentation source materials and microbial vouchers.

Sample Data. Designed for management of data on all samples (marine, plant, microbial) collected, specifically, to track tissue sample shipping, storage and handling prior to chemistry.

Chemistry Data. Designed to track development and handling of a sample through bioactivity-directed isolation. Requires different screen-forms for extraction (6 extracts and/or partitions/tissue sample), fractionation (80 fractions/extract), isolation (further fractionation and separation); with links to characterization data (spectroscopy, chromatography) and biological activity data at each step of development that exist in the form of raster-scanned images.

Biological Activity Data. Designed to track development and handling of a sample through bioactivity-directed isolation, and to navigate the user through the system on a course that is complementary to that which tracks the sample through chemistry.

NAPIS uses the sample number and suffixes to establish the links (indexing) between all records.

The NAPIS numbering convention is a composite number including a project prefix, year, month, day, site, and sample. The number can be extended to include an extract and fraction suffix. For example:

W199408020101FA01

The number is automatically generated and presented in a dialog box to the user when entering into a new form, the number is modifiable in the dialog box but is automatically enters into a restricted field in the established forms. Numbers will be printed by the system for affixing to sample/specimen containers using traditional methods and bar-code recognition technology.

Also considered are methods required for users to transfer information between the system modules: NAPIS Core, NAPIS Laboratory and NAPIS Remote. There are additional requirements for transfer to other database systems; for example, the NCI Contract Collectors transfer data to the NIH Drug Information System. To make these data transfers easy the function will be automated and implemented "behind the scenes", for example, users will select: file . . . ; utilities . . . ; prepare transfer to NAPIS Core . . . ; transfer data. To make these data transfers realistic the system database structures and transfer protocols will be designed using only simple field types (e.g., alphanumeric, number, date, sample) and will avoid use of complicated field types (e.g., memo, formatted memo, binary large object, graphics).

Receiving data at the NAPIS Core that is uploaded by system users will be handled using methods that protect data integrity within the core system. Uploaded information will be held in a "information received" section for review by System Administration and approved for addition to the information repository.

Digital Image Handling of Organism Photographs is discussed in the Significance Section and requirements were determined during the Phase I study; conclusions and recommendations are noted above. Digital images are, and will continue to be, critical elements of the NAPIS concept.

NAPIS allows "realization" of available image handling technologies. Images that are useful to biologist's when performing typical database searches are different than images required for critical analysis of a target organism. The NAPIS solution offers both. When performing database searches it is adequate to use the color bar and/or the reference to the Pantone (R) Color communication standard according to specifications described in the next paragraph. When a high resolution true-color image is required (a high resolution 24 bit color 35-mm slide scan can require a 25 megabyte file size) users can request this from the system; this is a manual function and other users that are the source of the image may be required to supply the original or a digital file that meets the higher specifications.

For images stored and linked to database records we plan to use JPEG compression. This format is acceptable for the black/white raster scans of, for example, NMR data linked to Chemistry Data records and for activity profiles that are linked to Bioactivity Data records. We also specify JPEG for storage and effective transmission of photo-real specimen images that are linked to the Specimen Data Files, with image capture automatic white-point/black-point settings and forced linear gamma curve. The first embodiment determined that 4"×5" specimen image dye-sublimation printouts that adequately meet most biologist's requirements are roughly 4.3 megabytes (24 bit color) before JPEG compression (20:1) to yield a file size of 502 kilobytes for effective storage. Data integrity of a JPEG compressed file or a 24-bit color format file is maintained wherever the image should be copied or transmitted (including Internet transfers).

Capturing and saving digital images of organism collections by users for NAPIS must conform to the discussed requirements specifications. Images are available using the JPEG glossy compression scheme at a 20:1 ratio. JPEG is not the best mechanism for maintaining true-color levels of an image since much of the data is discarded in the compression phase, however, it is acceptable (Nikon, 1994).

Meeting true-color image specifications is difficult. This is chiefly because an original scan uses the subtractive color model, whereas, electronic displays, in contrast, use the additive color model. These color systems are inherently incompatible, but much is done in computer software to minimize the differences. It is important to start with a clean, accurate source. This means calibrating the original scanning equipment with set color levels. Since the data is stored in a 24-bit (or 32-bit) format, data integrity, and thus color-integrity, is maintained wherever the file should be transferred. However, to insure that the document is viewed accurately, the viewing equipment must be calibrated as well (gamma, ambient light, white points, etc.). Unless there is complete control over the viewing equipment, some trueness to color will be compromised. PC equipment, and probably those using Mosaic viewers will be suspect.

Synchronizing colors with known quantities is a way of using a base reference point for matching colors between their source and their final destination. While the data is an accurate representation, the view is not. By using known industry-standard quantities for colors such as Pantone, individual colors can be referenced no matter how off-calibration the viewing equipment is. An important difference is that Pantone consists of about 1000 individual color swatches, whereas, the additive color model used in displays and digitization (RGB), can refer to 16.7 million different colors (24-bit). So only a fractional number of reference points can be utilized. This is particularly difficult with sources that contain continuous tones, like organism tissues. Solutions to these color-integrity issues can be provided by transmitting a file associated with the source image that contains the Pantone/RGB matching table; or to use the TIFF file format which can contain data not part of an image, yet associated with an image (such as a Pantone (R) Color table).

In most cases the NAPIS solution will provide investigators with a real solution that satisfies immediate needs for specimen recollection or dereplication. NAPIS specification digital images can be edited for close, but not formally true-color, matching to nature. Despite any technical shortcomings, this solution offers a standard for organism color communication and reference that updates the existing methods of assigning a color name from the Munsell Book of Color (faded circa. 1960's version available at most field stations), for example, or subjective descriptions like "periwinkle" or "salmon fizz".

Amplified PSDE also makes use of "graphical interface" technology for creation of "custom checklists." As described in the Significance Section, there is a need to create custom taxonomic hierarchical checklists that are built from the bottom-up. In developing this feature we plan to present users with an opaque interface that provides tremendous power and flexibility. Creating a custom taxonomy will begin with a traditional database query to group organisms at the genus level. With the groups defined, links will be established between taxonomic levels using "click and drag" methods to create any taxonomic structure; this feature and supporting technology resembles the capabilities of File Manager in Windows. Users will be able to store these custom checklists along with the system's "standard checklist" and default alternatives, and to assign them names like "gd_thur1.psd".

PSDE also includes links between an organism and its "range of species occurrence" in the GIS. NAPIS will generate a mapped boundary and coverage (mapped boundary with assigned attribute and table linkage) for each organism (conceivably) in the standard checklist. The number of organisms checklisted will easily exceed 100,000 for the second embodiment, and, while only a fraction will have an established link to a GIS coverage, it is obvious that the system design will have to consider large numbers of coverages. The system will automatically, but with System Administration approval, update a coverage when new information shows extended range.

Extended Advanced Technology Pilot Study-Mapping/Geographical Information System functional requirements seek to define the precise role of GIS technology as applied to natural products drug discovery and to biodiversity inventory projects; and to keep step with the rapid pace of technology advancement. A capable software system is required for networking and for handling the large datasets. The second embodiment defines specific GIS requirements for NAPIS support and develop an interface that includes only those features. These general requirements are:

Natural products drug discovery efforts require only to place points on a grid and show overlaid relative features to meet the needs for recollection, dereplication and expedition planning. Overlaid vector and/or raster data must be scaled, rotated, transformed and deformed (warped) to different map projections. GIS spatial analysis is required in some cases as well as GIS grid analysis. In scale-up, consideration of biodiversity inventory project development requirements will also be appropriate.

Biodiversity inventory projects require these and additional capabilities to perform soft-copy photogrammetry for terrain modeling, slope analysis, and extended modeling and image analysis of aerial photographs (including multi-channel spectral scan), to define resource boundaries.

Again, results of the Mapping/GIS Pilot Study will be incorporated into a standard work-flow protocol that is appropriate for use by natural products investigators and/or biodiversity inventory projects.

Data Requirements

Amplify the PSDE with updates to the "standard checklist" that is based on the National Oceanographic Data Center (NODC) Taxonomic Code. In the first embodiment, the NODC Taxonomic Code was embellished and implemented in the system; the updated information was provided to the NODC for their internal updates, which is common practice. The second embodiment continues to use the NODC Taxonomic Code as the standard checklist. The NODC dataset is provided in ASCII format and is easy to import, the taxonomic code itself is a 12 digit numerical hierarchical coding system that is presently intact, but will change within two years to adopt a random numbering scheme because the hierarchical system has become unmanageable and obsolete. This change does not create problems for use by NAPIS. While the system can encompass both marine and terrestrial environments and the NODC dataset includes marine and terrestrial organisms, the second embodiment concentrates on embellishing the PSDE marine organism features.

Spatial data (maps) can be obtained from published sources that document the "range of occurrence" for marine organisms and terrestrial plants. These data can be captured by digitizing the mapped boundaries for inclusion in the GIS. Published sources containing maps typically include comprehensive reviews on the flora and fauna of specific regions.

Additional features may be added to the system to address biodiversity issues, for example, information on endangered species as determined by the Convention on International Trade and Endangered Species (CITES).

Access to Commercially Available and Other Databases is possible with links on genus species names, the NODC Taxonomic Code, and with CAS Registry numbers. These databases primarily include the STN International NAPRA-LERT database, Berdy, MarinLit, NIST/EPA/MISDC Mass Spectral database, and Aldrich FT-IR Libraries.

Extended Advanced Technology Pilot Study Mapping/ Geographical Information System data requirements seek to define the appropriate technologies for assembly of base map data to be used in natural products investigation and/or biodiversity inventory projects. The following technologies are appropriate for consideration:

Global Positioning System (GPS) survey control at sub-meter confidence levels for map georeference
   GPS derived route tracing for delineating natural resource features
      World Geographic System 1984 (WGS84) datum based on an ellipsoidal reference system
      Aircraft-based multi-channel spectra-scanning, to support image processing
      Digital raster and vectorized map overlay
   Use of other appropriate spatial data from local and regional sources, including those acquired through the National Biological Survey and the Nature Conservancy.

Aircraft-based multi-channel spectra-scan data are available from the Washington State Department of Natural Resources. Old data that is not georeferenced (1988) exist at the present time.

Operational Requirements

Figure 4:
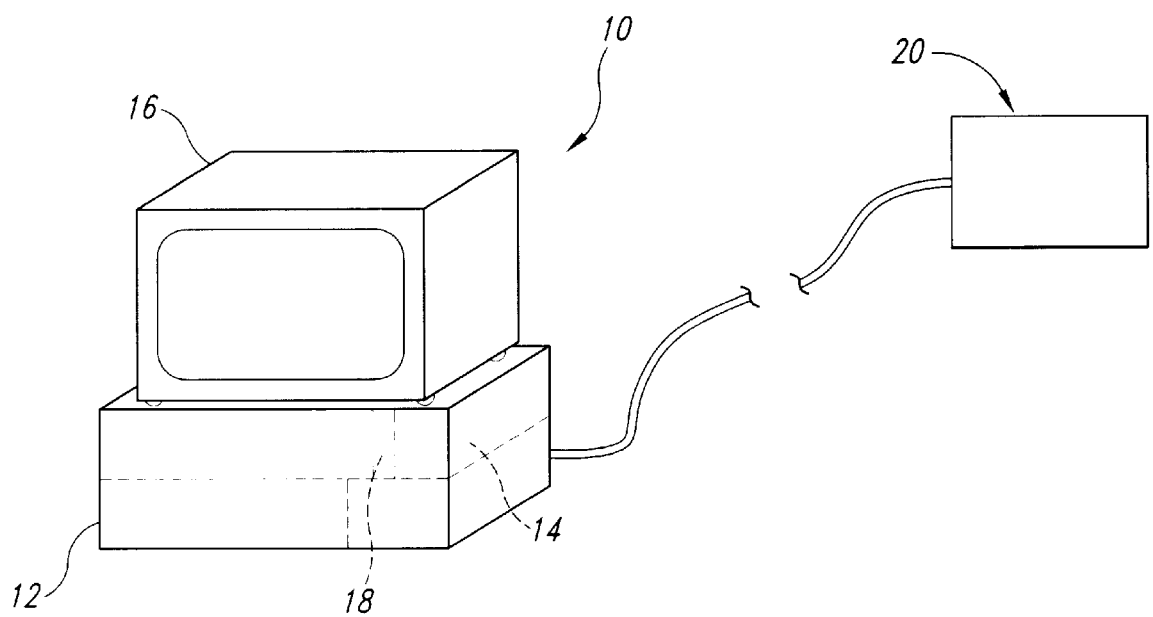
FIG. 4 is an illustration of a computer-based implementation of the present invention.
Figure 5:
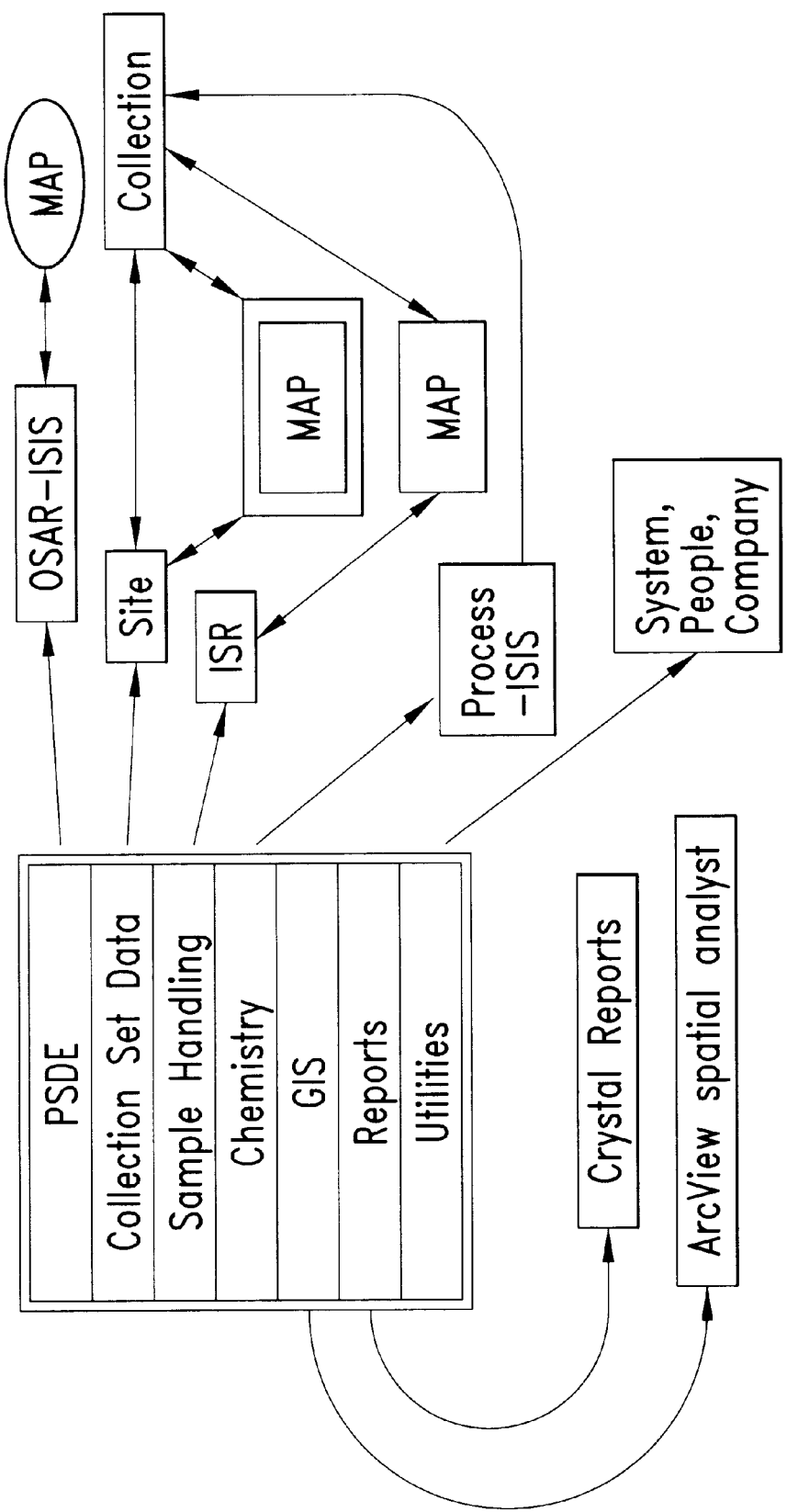
FIG. 5 is a diagram of the logical design for the present invention illustrating the correlation of the system of the present invention to existing sources of information and the output generated from the correlated data.
Figure 7:
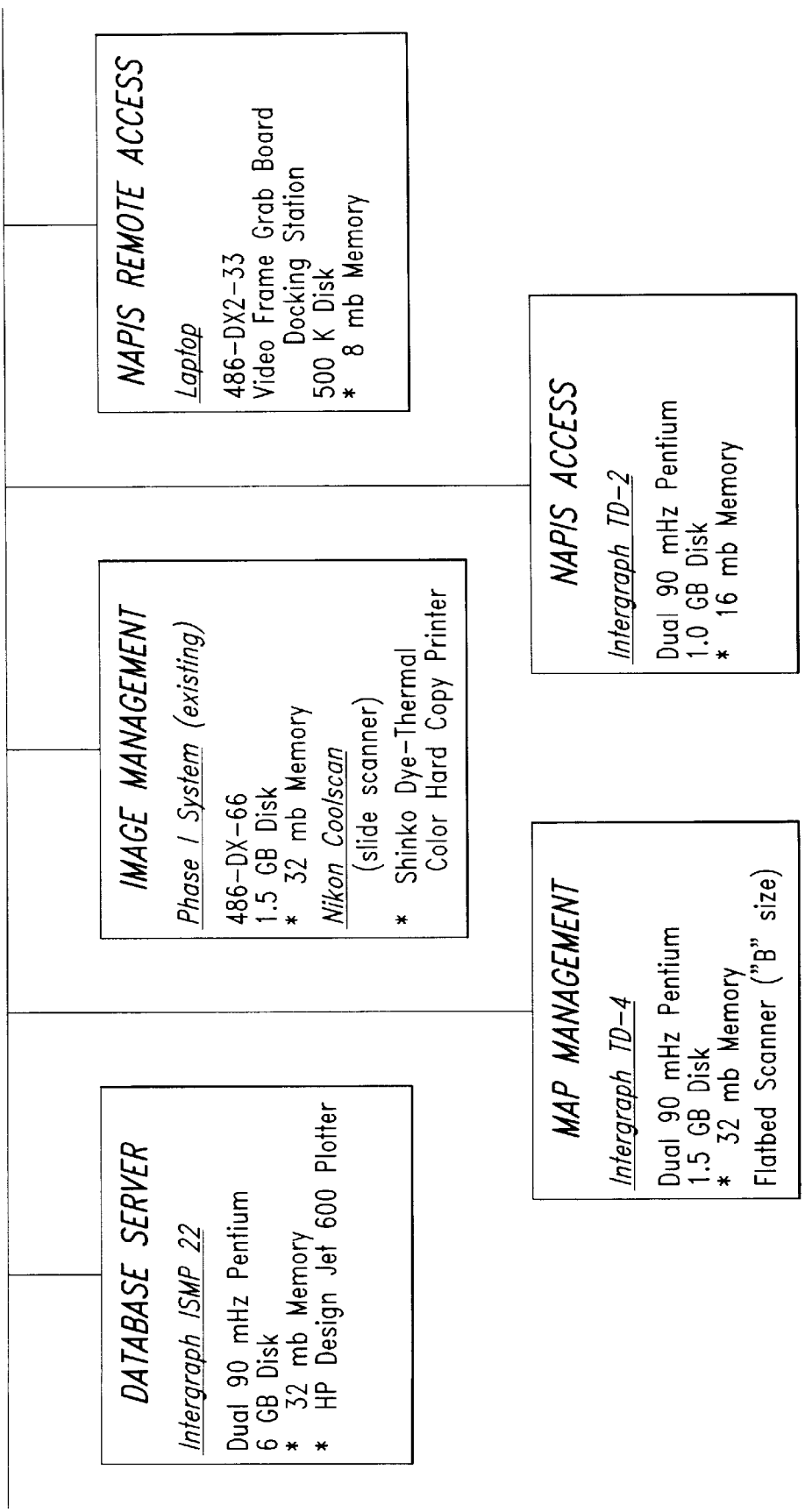
FIG. 7 is a block diagram representation of networked computer hardware

FIG. 4 illustrates a typical computer processing system 10 for use with the present invention, including a computer processor 12 having a memory 14 associated therewith and a display terminal 16 operatively connected thereto. An internal modem card 18 or equivalent may be used for communication between a computer processor 12 and remote databases 20.

a. System Software Requirements for the second embodiment or the Phase II Project include these Intergraph modules: MGE Basic Nucleus, MGE Basic Administrator, MGE Base Mapper, MGE Projection Manager, MGE Analyst, MGE Grid Analyst, MGE Map Finisher, MGE Terrain Modeler, MGE ASCII Loader, IRAS/C, ISI-2, dbaccess, Microstation 5.0 System Hardware Requirements for the Phase II Project include a TCP/IP network system (Internetready). This is illustrated in FIG. 7.

b. NAPIS Logical Design

The NAPIS Logical Design shown in FIGS. 3A and 3B is independent of the application software and is based on the application requirements. The NAPIS Logical Design schematic is based on the first embodiment and extended to include three Data Record forms. It was developed with consideration for hardware, software, data transfer and workflow.

C. Risk Analysis

Data Transfer

NAPIS development using Intergraph technologies is, at the present time, the only way to implement the system. Intergraph client-server network capabilities for resource allocation of system-intensive GIS and image handling requirements make NAPIS possible. Data transfer requirements, however, may slow the system's performance to an unrealistic level because of Windows NT based application band width requirements for data transfer. For example, while the on-line requirements for displaying the GIS program application that runs on the core along with vectorized linework are reasonable, to display an 8-bit color raster overlay of a topographic map will slow the system and display of a 24-bit color raster multi-channel spectral-scan for image processing will slow the system further. System design and implementation considers these data transfer intensive requirements by running applications on the client system (NAPIS module).

Data Conversion

Implementation of a database is decidedly dependent on data specification and data conversion between the elements of the system. Data collection, conditioning, and conversion are considered to be the Achilles' heel of many projects. The NODC Taxonomic Code has been identified as important.

Data conversion and conditioning typically consider, for example, entry of dates and of geographic positions. As discussed above, the NCI receives data using different entry styles. Once the entry of this type has occurred, any editing must rely on the quality of metadata that supports it as a dataset. These issues decidedly plague database projects and can only be adequately addressed on a case by case level. NAPIS design standardizes the connectivity that it offers to other databases, using genus species (as a paired index) names, CAS Registry No. and NODC Taxonomic Code, by using standard datasets.

V. Systems Screen Shots

Turning next to FIGS. 6 A–P, shown therein are screen shots from another embodiment of the present invention.

Figure 6A:
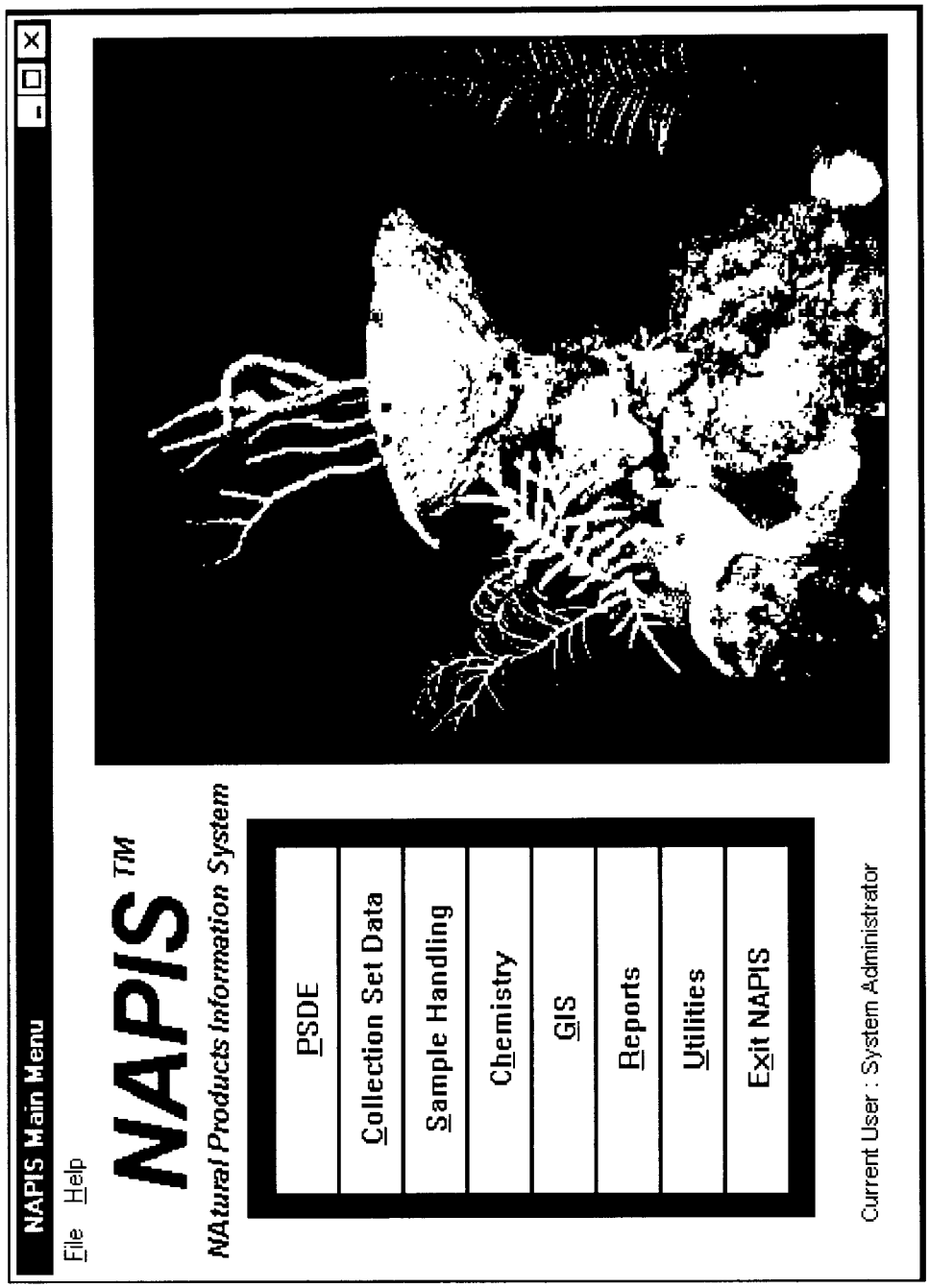
FIGS. 6A–P are screen shots illustrating the processing of natural products data, natural products image data, and the correlation of such data, including correlation with remote information sources.

FIG. 6A shows the NAPIS main menu for navigation to the different modules. These modules are the PSDE Collection Set Data, Sample Handling, Chemistry, GIS, Reports, Utilities, and Exit NAPIS. FIGS. 3A–3B show the logical relationship of these modules.

Figure 6B:
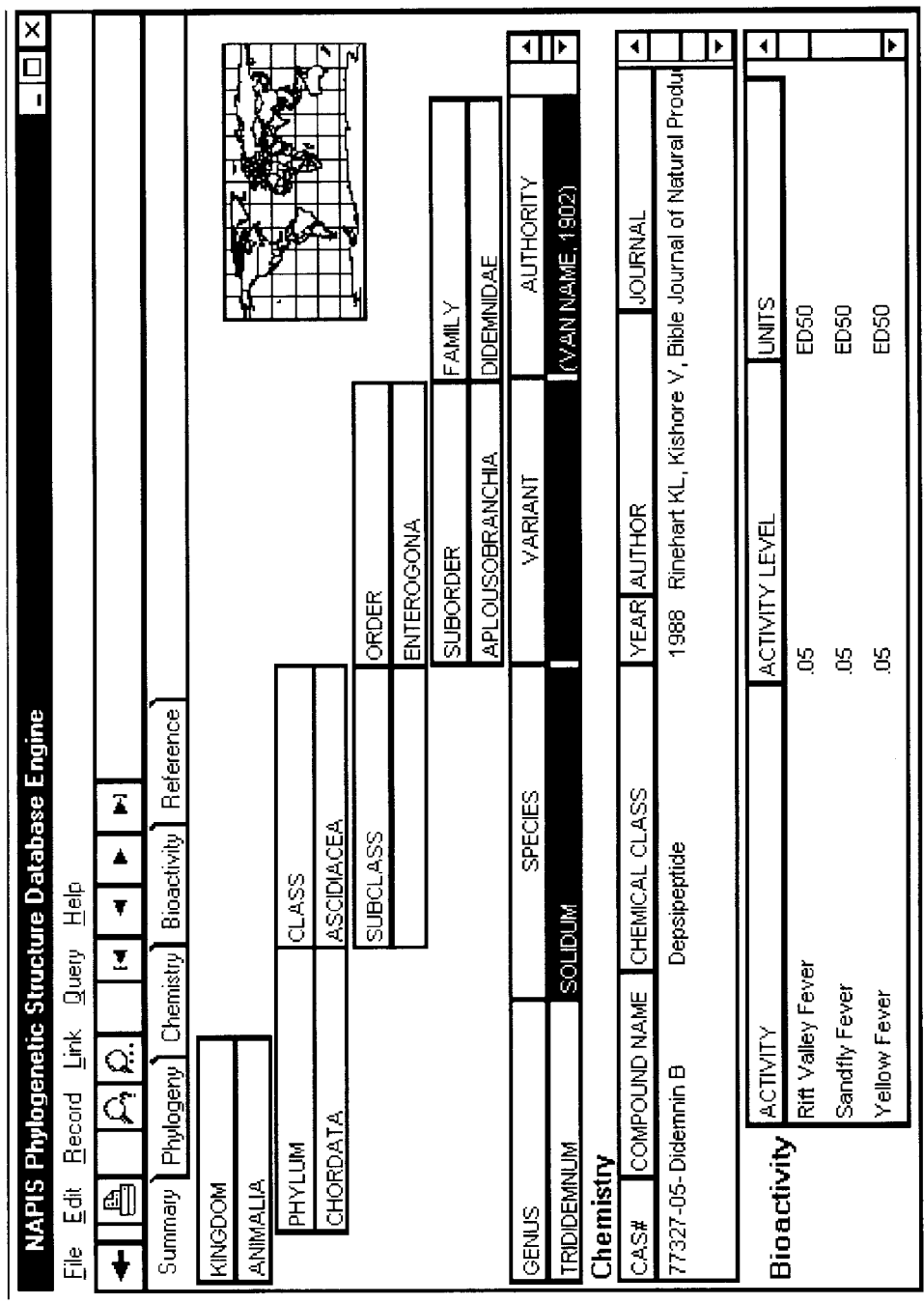

FIG. 6B is a screen shot of the PSDE Summary tab form. The NAPIS higher taxonomy is displayed with NAPRA-LERT chemisty and activity data. Query of the NAPRA-LERT (or other commercial database) is available at higher taxonomic levels using NAPIS assignments.

Figure 6C:
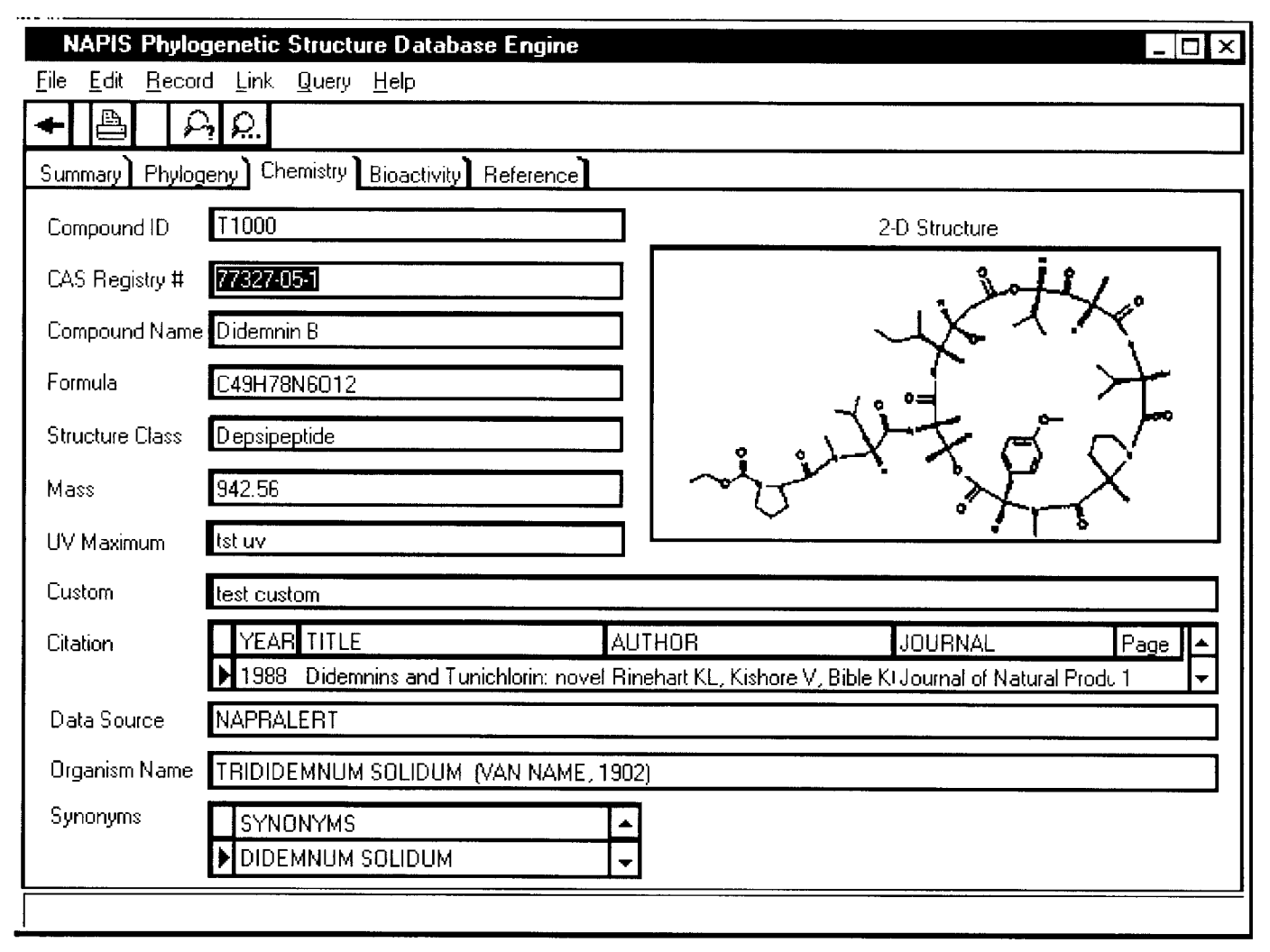

FIG. 6C illustrates the PSDE Chemistry tab form. The NAPRALERT data with ISIS/Base OCX vector chemical structure is shown. Users can query by attribute or compound substructure and display the query result on the map, making it available for later-stage GIS query.

Figure 6D:
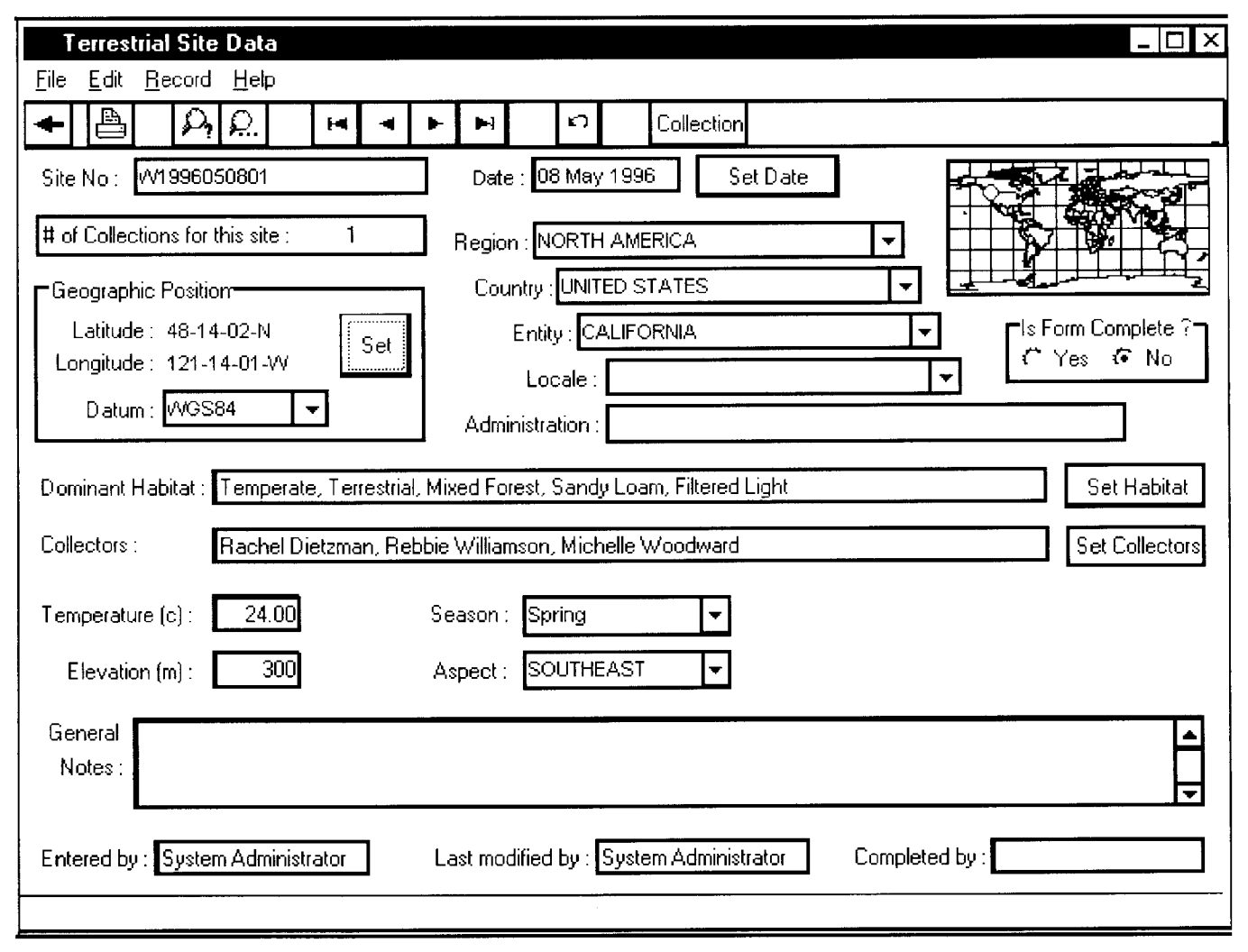

FIG. 6D is the Collection Set Data, Site Form. This is used for entry of the geographic position and streamlined entry for geographic location, habitat, collectors, etc. Double-clicking on the map brings up a larger GIS-based map interface. Collector and system users are administered at the system level through the Utilities module.

Figure 6E:
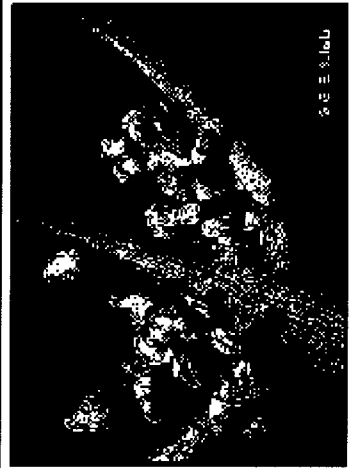

FIG. 6E illustrates the Collection Set Data, Plant Taxonomy tab form. Access to the GIS-based map is had through double-clicking on the small map. The emphasis is on standardized entry choices within NAPIS.

Figure 6F:
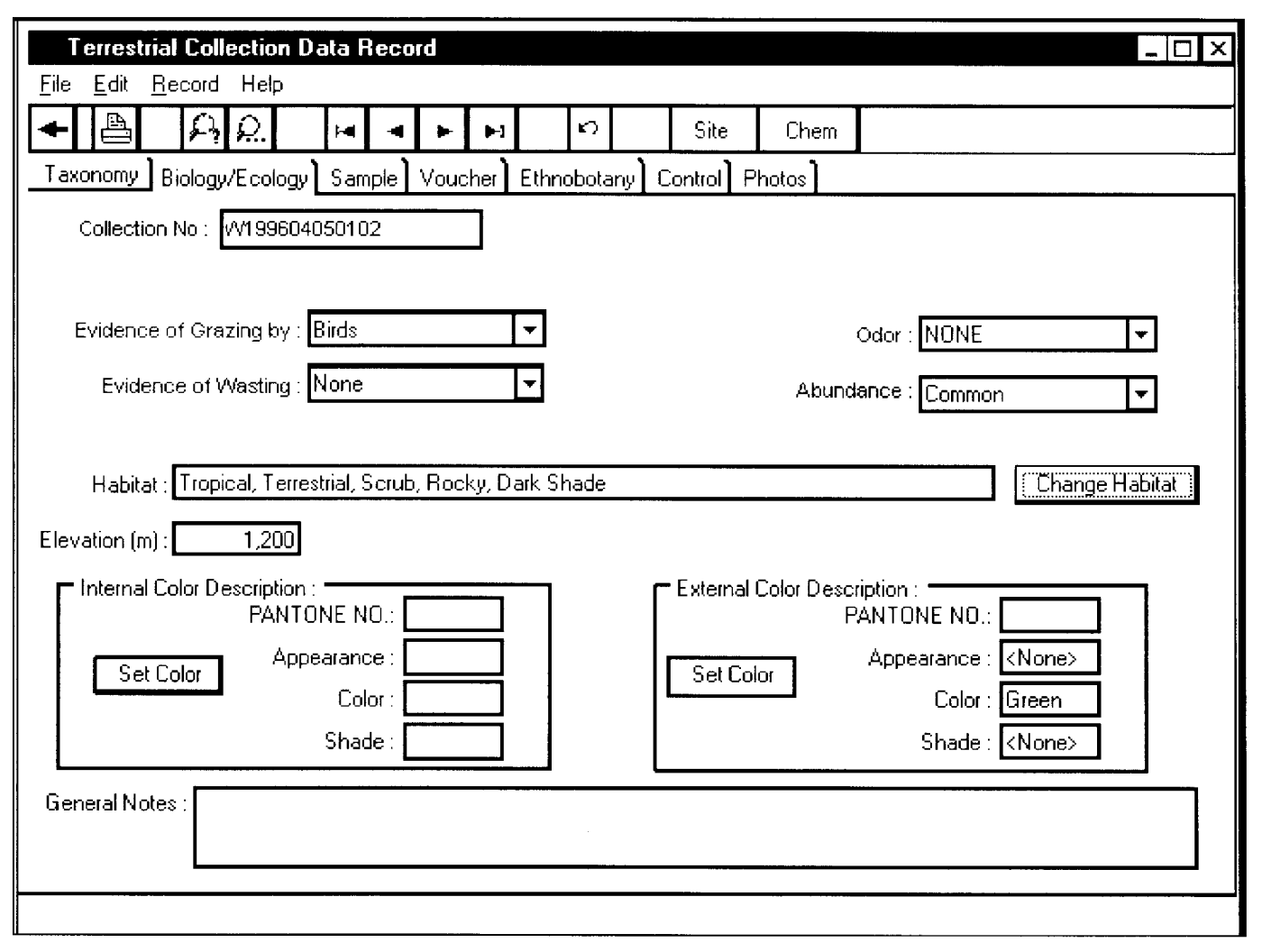

FIG. 6F illustrates the Collection Set Data, Plant Biology/ Ecology tab form. Standard choices are available for color communication and other searchable fields.

FIG. 6G shows the Collection Set Data, Plant Sample tab form. This is used for the many samples that correspond to one taxonomically distinct unit. Clicking on the Sample Submittal button will display FIG. 6I.

Figure 6H:
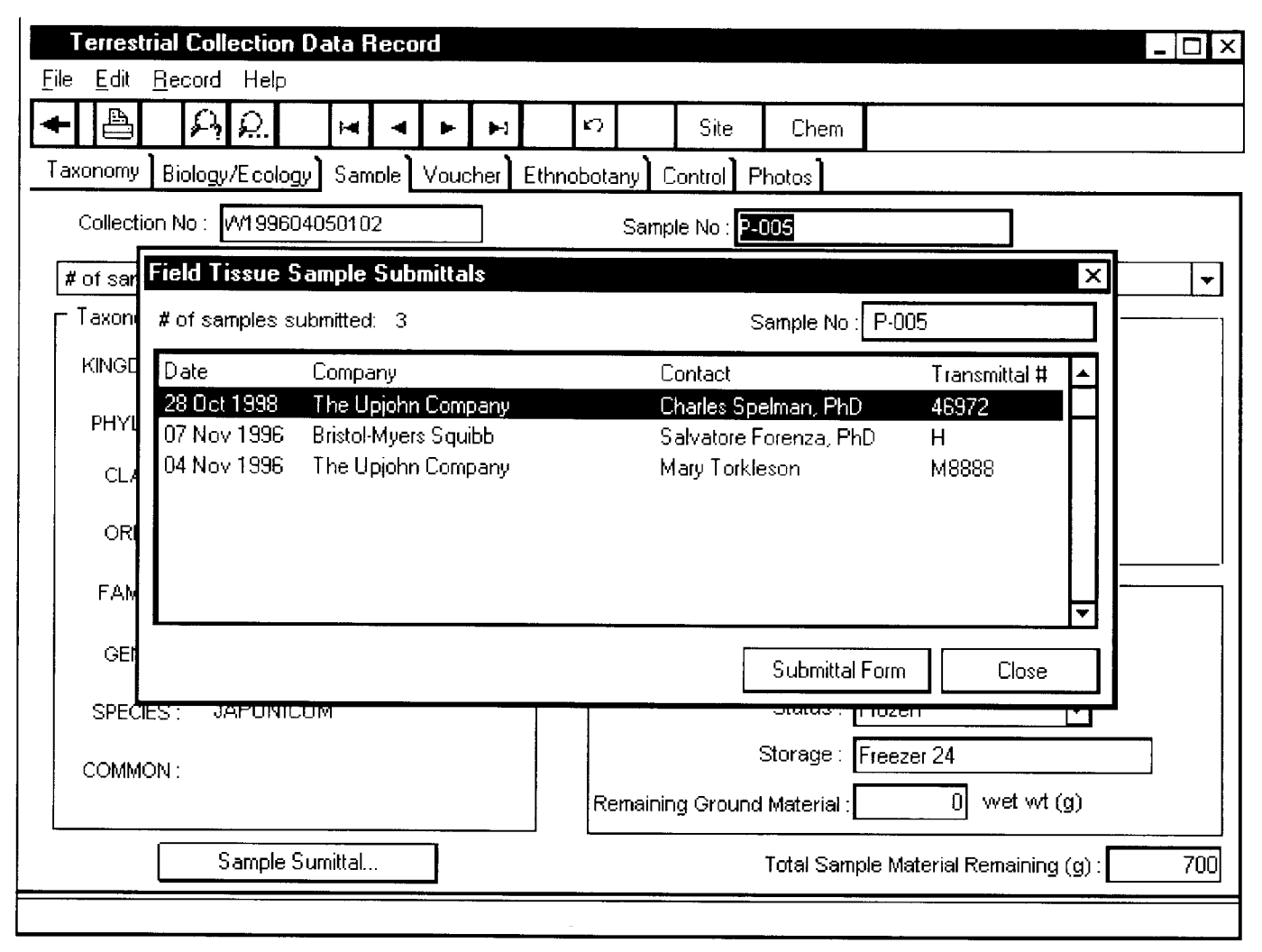

FIG. 6H is the Collection Set Data, Sample Submittal dialog. This shows a list of submittals. Clicking on the Submittal Form button displays FIG. 6J.

FIG. 6I is the Collection Set Data, Voucher tab form.

Figure 6J:
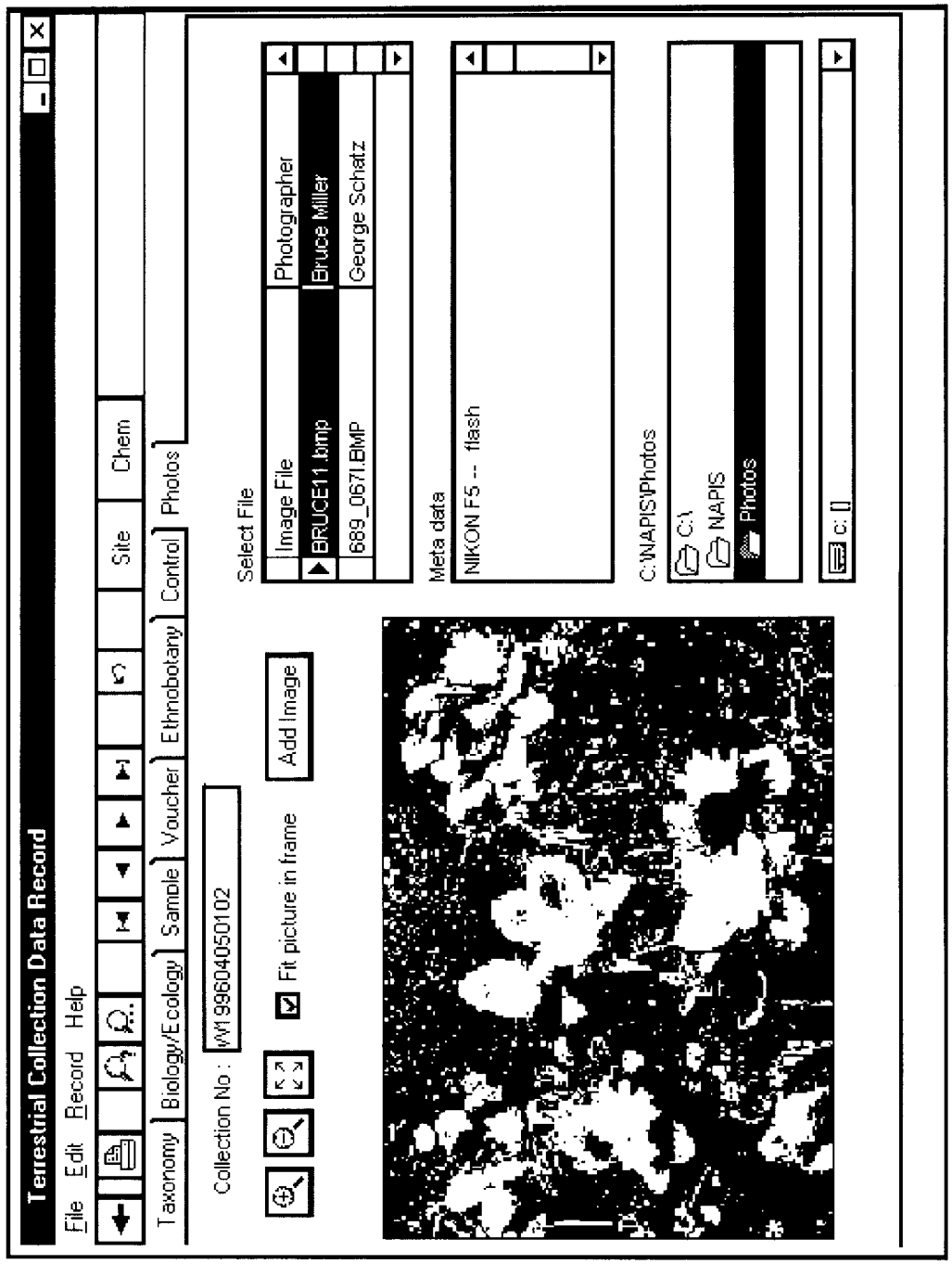

FIG. 6J is the Collection Set Data, Photos tab form. This can handle many photographs for each collection stored in different places.

FIG. 6K is the Sample Handling, Submittal Form. Users can navigate here from the example in FIG. 6I or from the main menu. This record corresponds to the choice in FIG. 6I. Note the Pie Chart and Site Map buttons for FIGS. 6K and 6L.

Figure 6L:
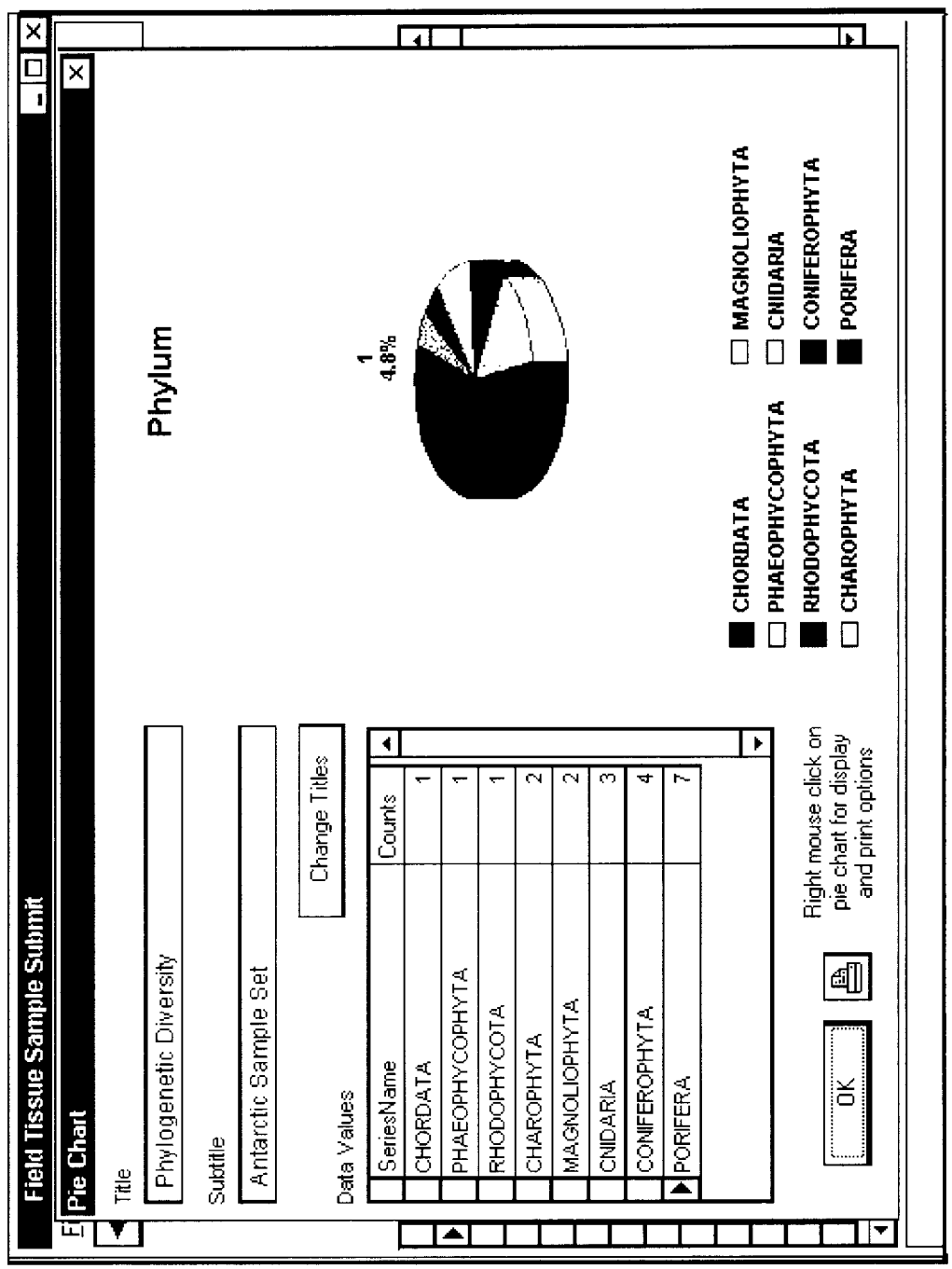

FIG. 6L is the Sample Handling, Submittal Form Pie Object OCX. This is created on the fly for the highlighted column.

Figure 6M:
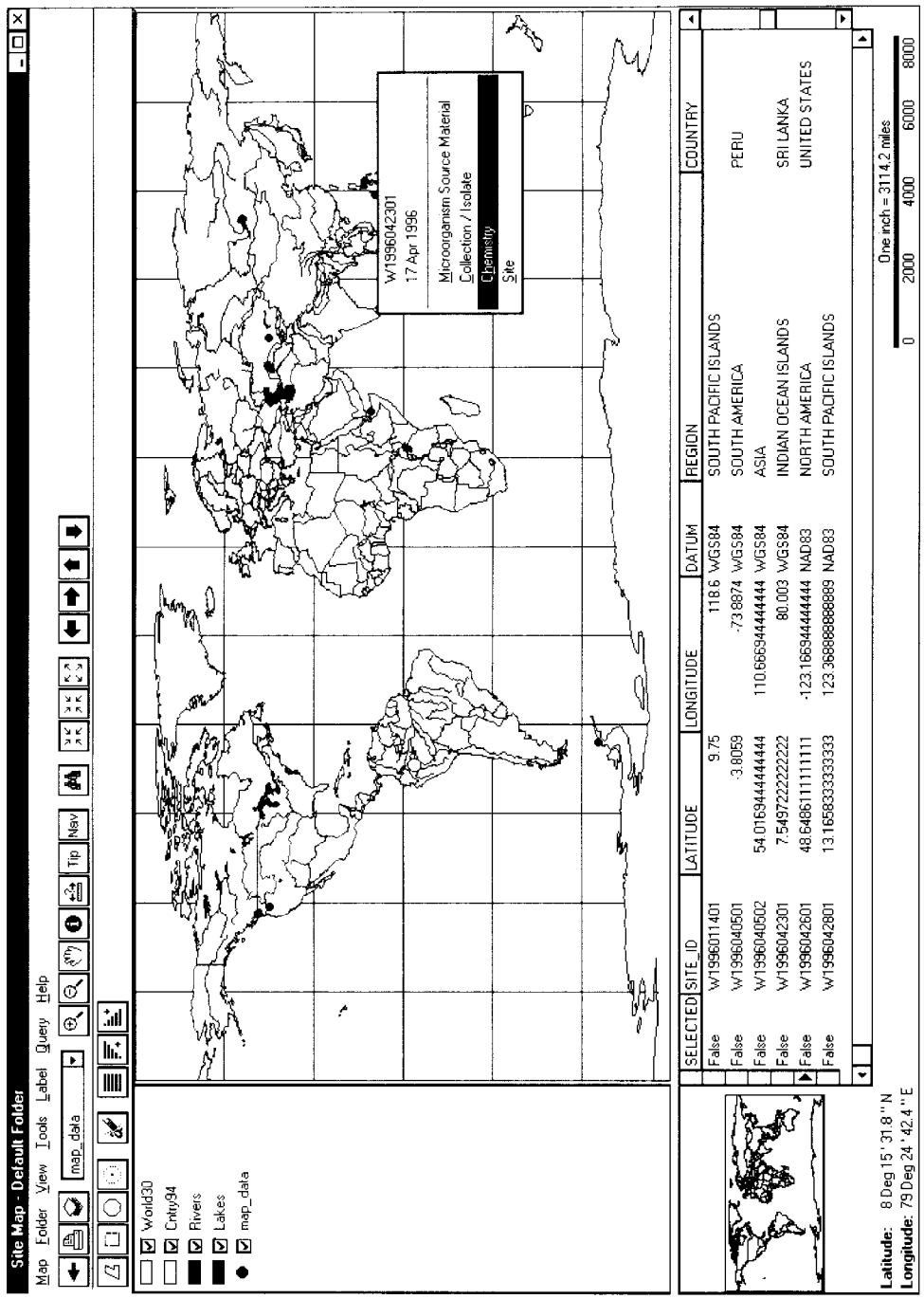

FIG. 6M is the Sample Handling, Submittal Form Map Object OCX. This is created on the fly for each record and has GIS functionality. This map is also called from the Site Form, Collection Form, and from within the PSDE.

Figure 6N:
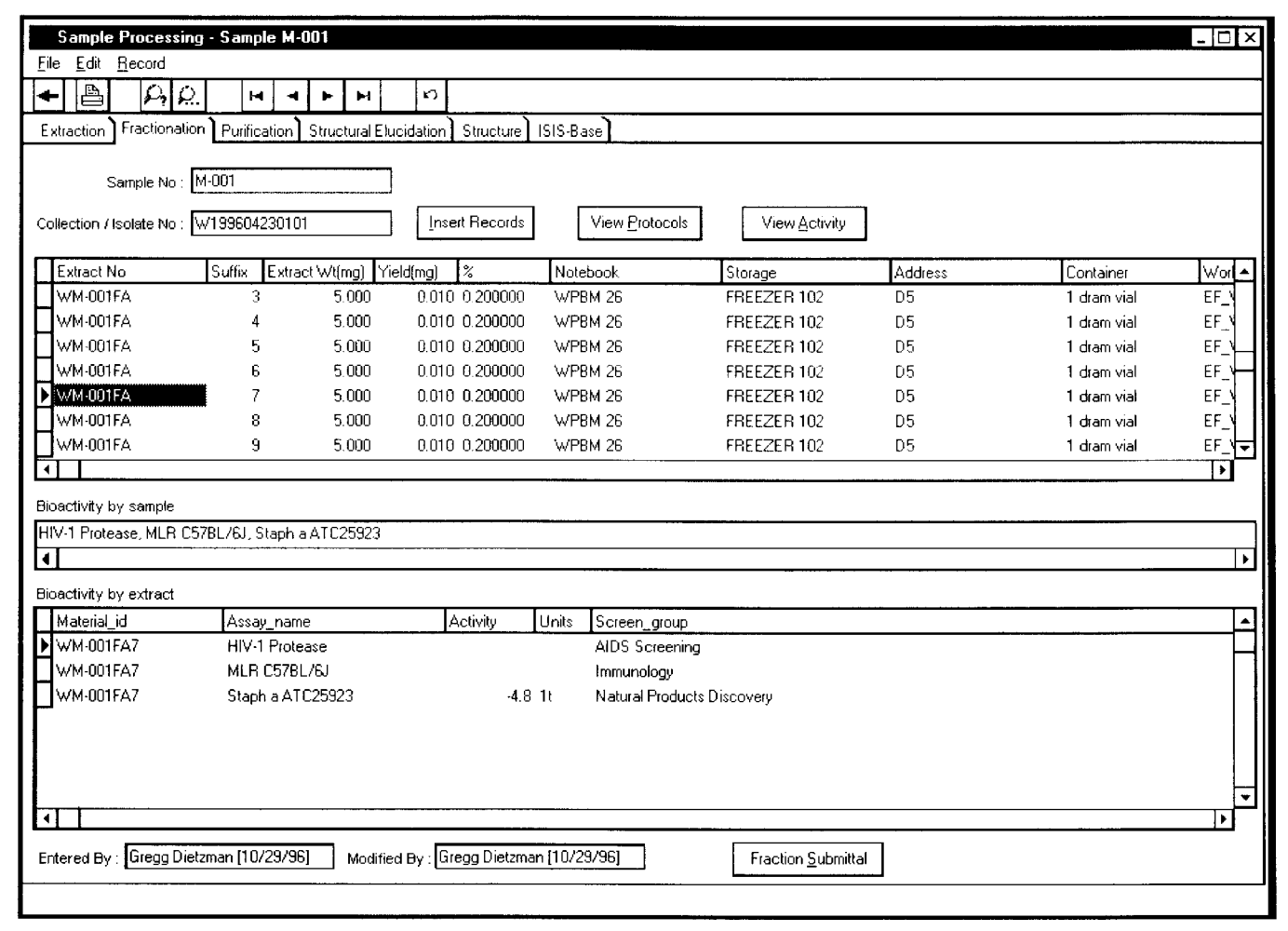

FIG. 6N is the Chemistry Sample Processing, Fractionation tab. The Chemistry module tracks the transfer and consumption of material quantities within the database, along with protocol designators. Protocols, however, are only described in the system. Protocol ID's are searchable. Recipes are not searchable. Also note the display of bioactivity by tissue-sample (middle list) and by chemistry sample (bottom grid).

FIG. 6O is the Chemistry Sample Processing, Set Purification Values display. For each initial Chemistry tab form there are dialogues for streamlined entry of grid values. Notice the pooled fraction entry method for handling the many-to-many relationship.

Figure 6P:
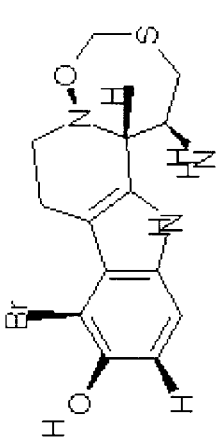

FIG. 6P illustrates the Chemistry Sample Processing, Structure tab form. This is the display of MDL, Inc. ISIS/Base database, including the 2-d vector-based structure.

Figure 8:
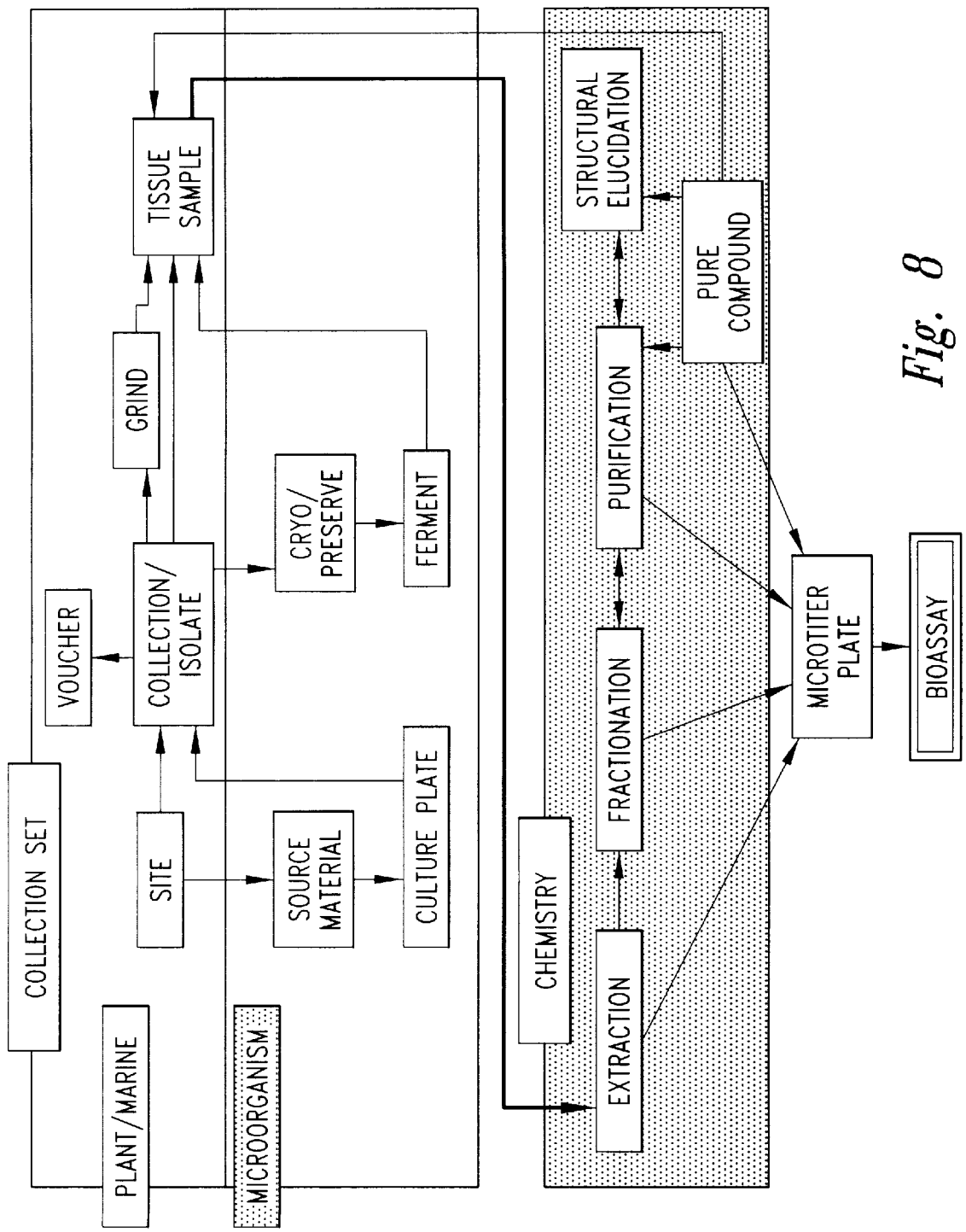
FIG. 8 is a block diagram representing the functional design of the data modelling concepts process of the present invention.
Figure 9:
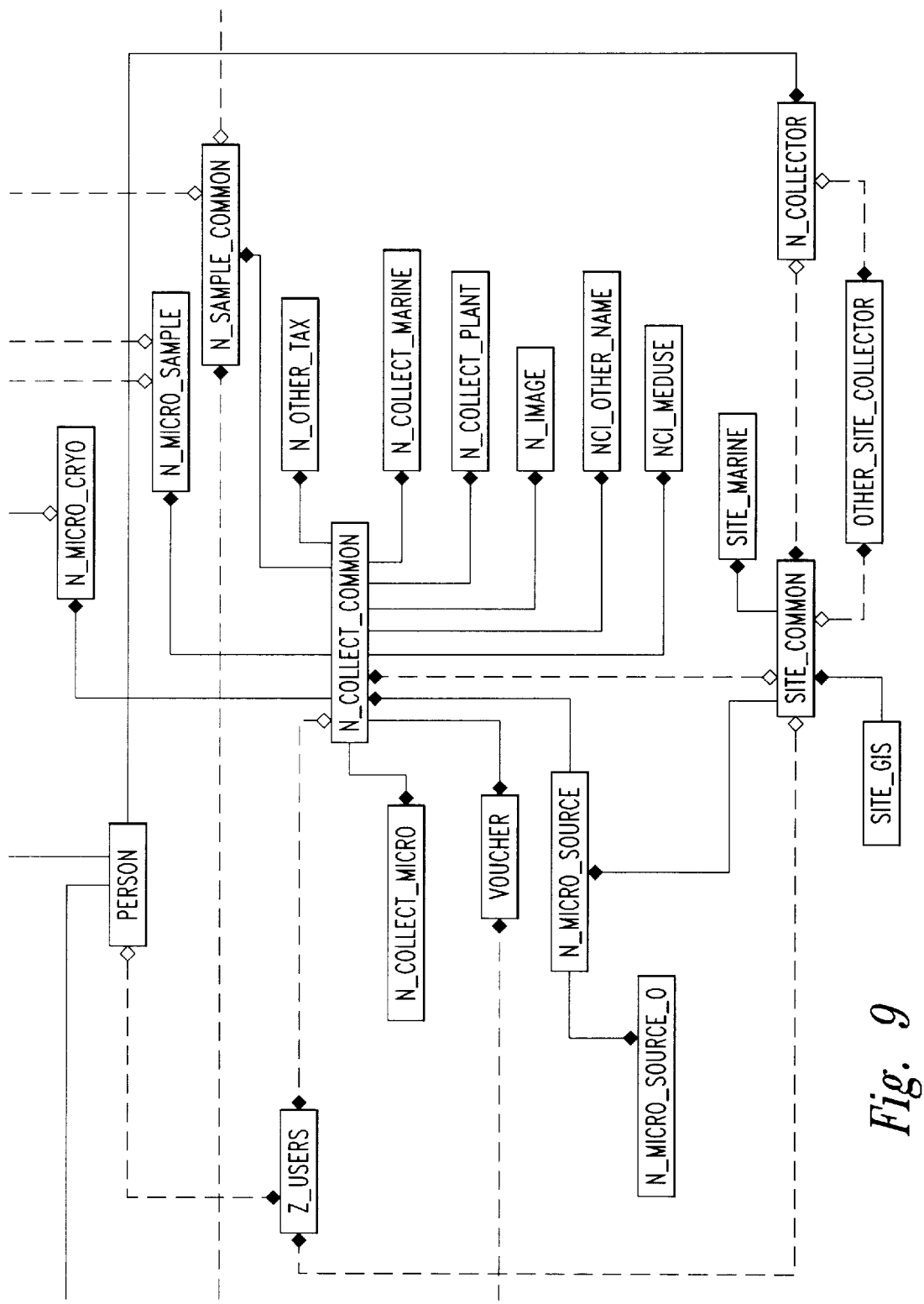
FIG. 9 is a block diagram representing the physical design of the Collection Set Data process formed in accordance with the present invention.
Figure 10:
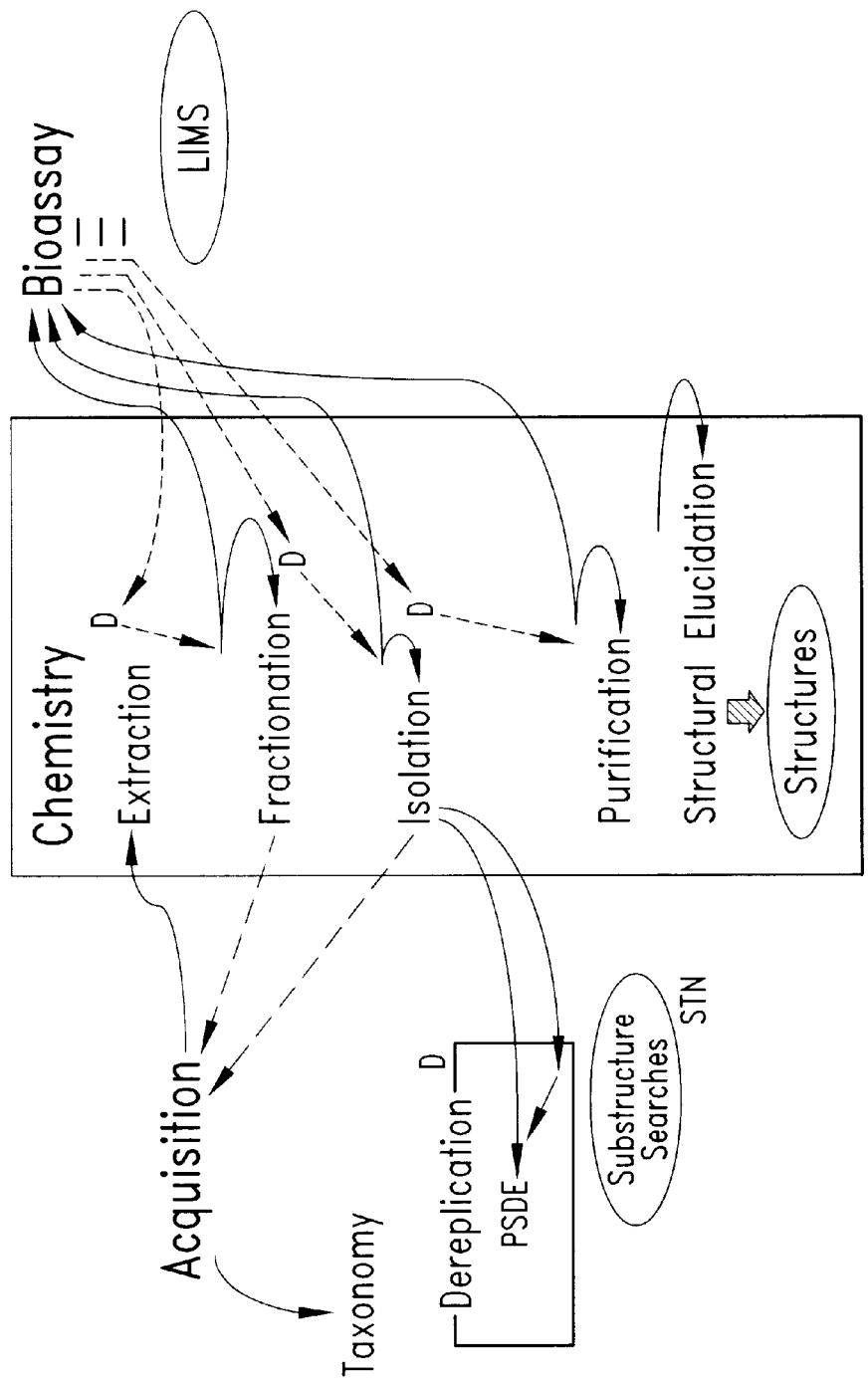
FIG. 10 is a block diagram representation of the functional design of the activity directed isolation Sample Handling process formed in accordance with the present invention.
Figure 11:
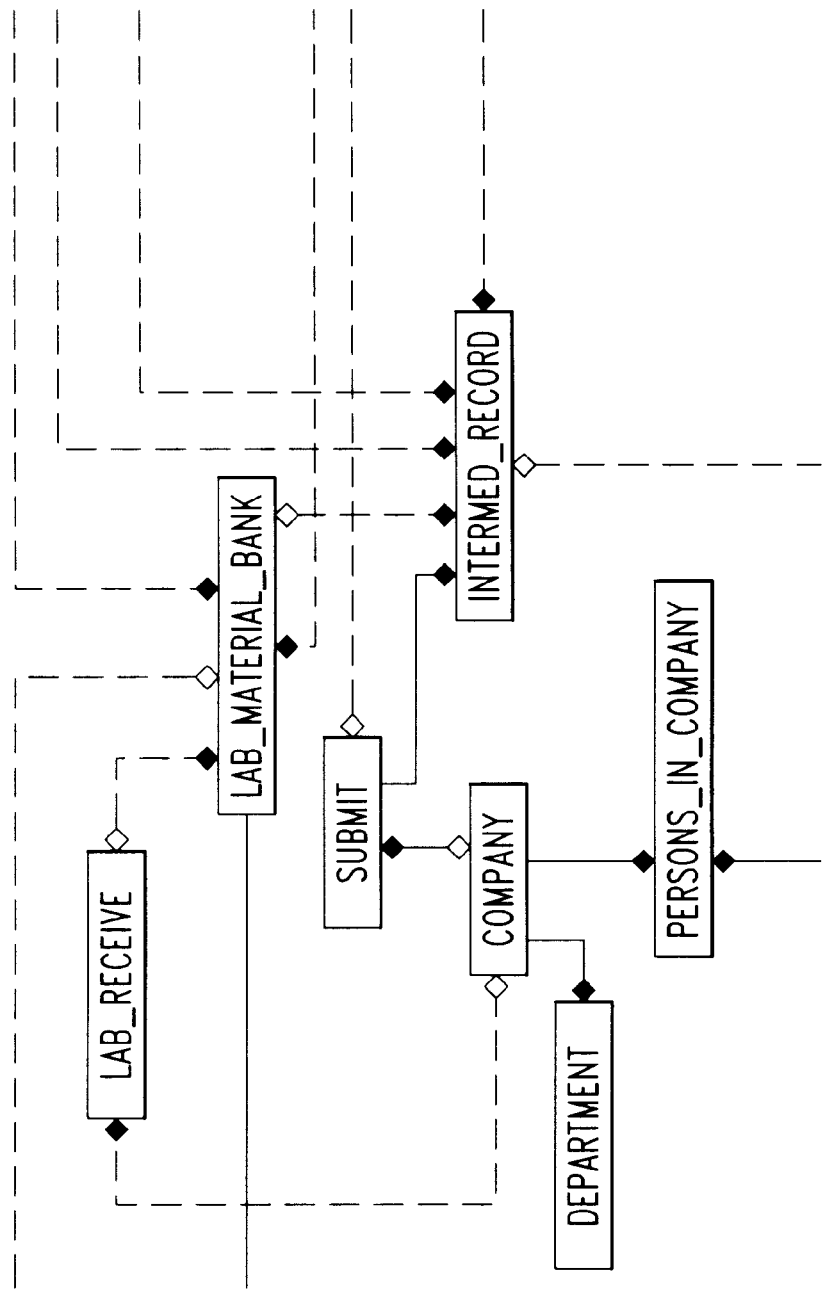
FIG. 11 is a block diagram representation of physical design of the Sample Handling process formed in accordance with the present invention.
Figure 12:
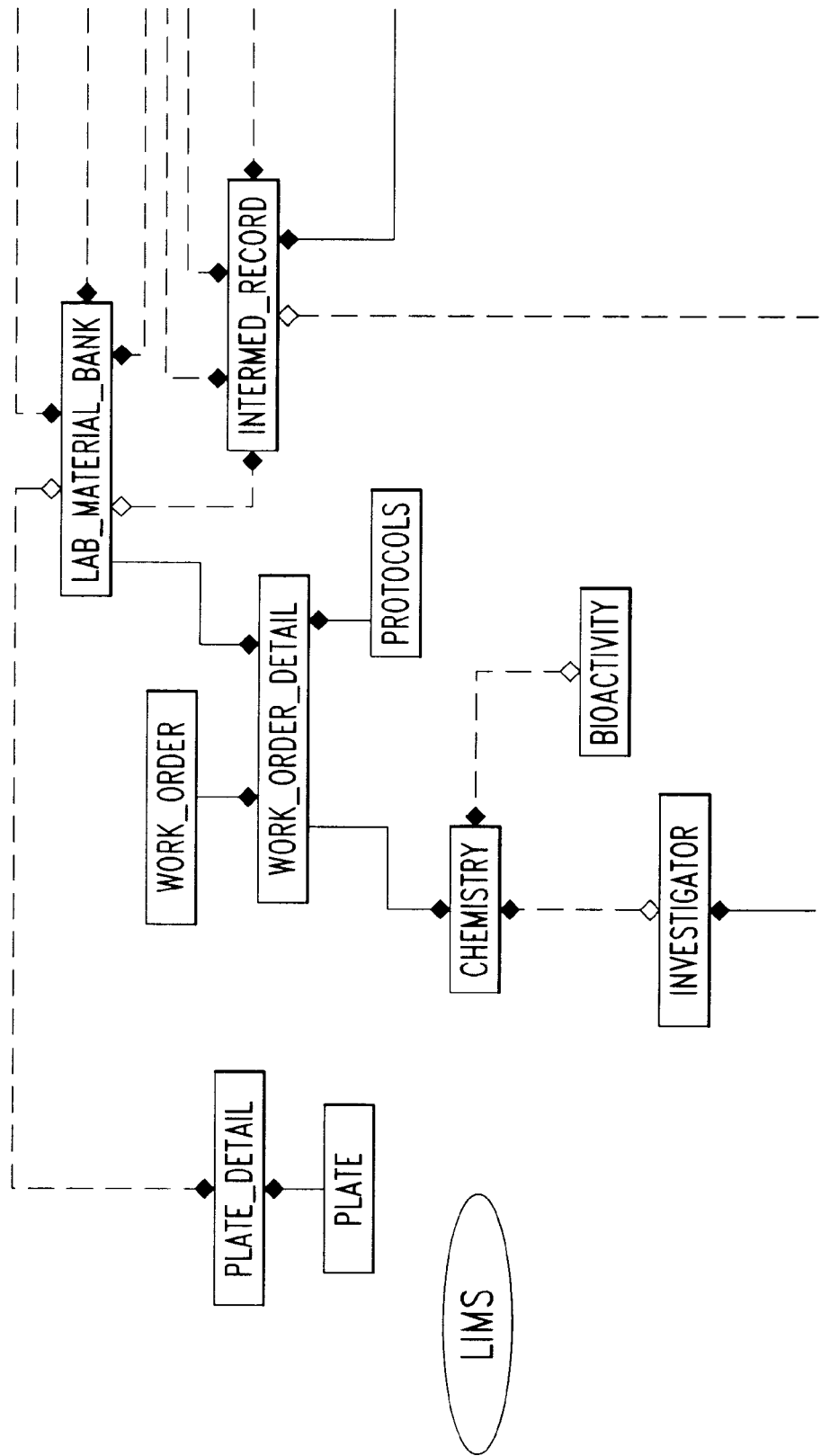
FIG. 12 is an illustration of the physical entity relationships of the Chemistry/Bioactivity process formed in accordance with the present invention.

FIG. 7 is a block diagram representing the various hardware configurations suitable for the described embodiments of the present invention;

FIG. 8 is a functional illustration of data modeling and correlation formed in accordance with the present invention;

FIG. 9 is block diagram representing the physical design of the entity relationship model;

FIG. 10 is a functional diagram of the activity directed isolation sample handling process formed in accordance with the present invention;

FIG. 11 is a block diagram representation of the Sample Handling—Physical Entity Relationships Process formed in accordance with the present invention; and FIG. 12 is a block diagram representation of the Chemistry/Bioactivity—Physical Entity Relationships Process formed in accordance with the present invention.

VI. Third Embodiment

NAPIS is developed using Borland Delphi v 2.0, ESRI MapObjects v 1.1, MDL ISIS Application Development Kit v 2.1, and SkyLine ImageLib v 4.0, can be delivered as three separate products:

NAPIS Enterprise—a full featured system that runs on PC's and networks with the workstation database ORACLE v 7.3 and the ESRI Spatial Database Engine. This product is designed for use by large organizations with aggressive discovery programs and includes advanced database security and administration methods that are consistent with electronic notebook concepts.

NAPIS Laboratory—a full featured system that runs autonomously or on a PC network with the desktop database Paradox v 7.0. This product is designed for use by organizations that require NAPIS functionality but do not require advanced database security and administration.

NAPIS Lite—a limited feature version that runs autonomously on PC's with the desktop database Paradox v 7.0. This product is designed for use in the field on laptop computers, has limited Sample Handling features, and does not include Chemistry.

Set for below is the feature-set and functionality of each system module, with discussions on specific related aspects of the system. Modules include:

PSDE (phylogenetic structure database engine)
Collection Set Data
Sample Handling
Chemistry
GIS
Reports
Utilities Set forth below is the description of how to sue a third embodiment of the present invention. The program installation is handled with an Install Shield where all of the components are copied to your computer and properly registered, icons are created, and the file structure is created which contains the database. The data tables are empty except for a login.

Installation

Install the copy of ISIS/Base and ISIS/Draw provided. This must be performed first for proper registration of NAPIS components. ISIS must be installed at the default location under c:\Program Files\Isis21. Even if your normal "Program Files" directory is on a drive other than C:, Isis must be installed on the C: drive in order for the current beta installation to install correctly. This will not be the case for the release). See the ISIS documentation. Please copy the attached letter to your letterhead (or generate one of your own) and send it to MDL—this is an important condition of the Beta Test Program.

Run Setup.exe found on the NAPIS—CD. NAPIS must be installed at c:\napis for the beta. Note that the checkbox must be checked at the end of the installation to complete the install. This selection runs a batch file for registering NAPIS components that will open a DOS shell that runs three scripts, click 'OK" for the dialog noting the success of each registration, then close the DOS shell. Icons are installed in the Windows TaskBar. Restart of the machine is required.

Copy the file system from the NAPIS—CD directory \napis_cd which includes the subdirectories: Data, GIS, Inventory, Isis, Lookup, Napralert, Photos, Receive, Submit, System, WorkOrder. Each of these subdirectories is required along with the complete set of data files. If the program gives errors writing data to the files, set the files in each subdirectory from 'read only' using the checkbox in Windows Explorer | File | Properties (affects highlighted files). Sample data files are found in the CD:\_sample directory may be copied if you choose. To uses these files, replace the files in the same name directories for Data and Photos.

Run NAPIS from the TaskBar. Type 'sa' for the login (=System Administrator)—this will take you into the NAPIS Main Menu where access to the different modules are listed.

First Steps

Create user(s) in Utilities | Personnel. In the 'Personnel Maintenance' dialog select Modify for 'Persons' to open the 'Person Data' dialog—select Record | New Record from the Menu Bar. Enter Company information in a similar fashion. Enter Setup/Preferences information in Utilities | Setup. Set choices for 'Lat-Long', 'Collection Number' and 'Site Number'. The 'Directories' settings default to the beta installation and the 'Station' information is not required at this time. You are now ready to enter data into NAPIS.

General Navigation through NAPIS

All NAPIS Modules are accessible through the Main Menu. Most of the Module screen-forms use form-tabs which bring up additional forms, except for Site Data and Microorganism Source Material Data. The forms have navigation tools found on the tool-bar, these tools are buttons with names like 'Collection', 'Chemistry' and 'Site' which navigate to the corresponding records in other forms. Each form has a title-bar, menu-bar and tool-bar, in addition to the general form functions. Windows conventions have been followed in the forms design and implementation—you should find many of the common keyboard entries for navigation and entry at each form. We have purposefully tried to limit the numbers of icons used. These are the general *-bar functions:

Menu-bar

| | |
|---|---|
| File | common functions |
| Edit | find and find next, same as tool-bar functions |
| Record | New Record and Delete Record, plus scroll functions |
| Preferences | variable |

Tool-bar

| | |
|---|---|
| Back Arrow | back to the previous form |
| Print | print form screen |
| Find | find value for selected field |
| Find Next | find next value for selected field |
| Scroll to First | go to first record in table |
| Scroll Previous | go to previous record in table |
| Scroll Next | go to next record in table |
| Scroll Last | go to last record in table |
| Undo Last | cancels edits since opening record-specific form |
| Navigation | navigates to other forms |

Forms design utilize many windows conventions:
check-box allows select of many from list
radio-button allows select of one from list
pull-down choice list select one value from list
button nav to dialogues accesses other dialogues
* lookup-table values are editable through Main Menu | Utilities | Lookup

PSDE

Feature Set:
PSDE is browse and query only.
Summary information is drawn from NAPIS for Phylogeny and from NAPRALERT for Chemistry and Bioactivity through a link between datasets on Genus species name as a paired index.
Phylogeny data from NAPIS tables, taxonomy and spatial metadata handling.
Chemistry data of selected Bioactivity from NAPRALERT linked to ISIS/Base.
Bioactivity data from NAPRALERT.
Reference data displayed for the selected Bioactivity from NAPRALERT.
Map implemented to illustrate display of proprietary (red circles) and non-proprietary (white squares) data in map form—refer to NAPIS-GIS for query examples.

The purpose of the PSDE is to link important non-proprietary datasets to NAPIS for assignment of higher taxonomy, which many of these datasets do not offer. It provides a standard interface to the different datasets and allows query at higher taxonomic levels (see Appendix 1, 2), for example, all compounds from a specific chemical class, with specific bioactivity, from the marine invertebrate sponge Order Poecilosclerida.

NAPIS version 1 will extend these queries to include a compound substructure and/or spatial (GIS) element. It will be possible to perform a substructure-based query and display the results on a map, or perform a GIS spatial analysis query and derive a subset of compound structures.

Implemented at this time for browsing is a "find" tool on the tool-bar of the form that can search on any field. For testing, review the records for Trididemnum solidum and Taxus brevifolia.

Supporting taxonomy data for the PSDE module is assembled from a series of digital datasets, the goal is to be near-comprehensive with emphasis on those taxonomic groups with known biomedical importance. This dataset will be extended for the version release.

The non-proprietary databases that we plan to link with include:
NAPRALERT
Chapman Hall Dictionary of Natural Products
Berdey
MarinLit
Emphasis here is placed on the NAPRALERT and Chapman Hall.
PSDE Form
Summary
Searchable at the field level using 'Find' tool
NAPIS taxonomy (upper half) links on paired index of genus species name to data in NAPRALERT database table structure (lower half)
Example data are: TAXUS BREVIFOLIA and TRIDIDEMNUM SOLIDUM
Genus species setting is maintained from tab to tab
Phylogeny
NAPIS Taxonomy, including 'synonomy' and 'common names'.
Taxonomy Source button calls 'Source Info' dialog with description of record source and navigation to metadata description (under construction)
Geographic Source button calls 'Source Info' dialog with description of record source and navigation to metadata description (under construction)
Chemistry
NAPRALERT data exclusively, except ISIS 2d structure and NAPIS organism name
Bioactivity
NAPRALERT data exclusively, except NAPIS organism name
Reference
NAPRALERT data exclusively, except NAPIS organism name
Map
Displays NAPRALERT points using Gazetter link with NAPIS points in different colors on same map (supporting dataset and code under construction)
COLLECTION SET DATA
Module Status: The Collection Set Data module is complete for microorganism, terrestrial plant and marine organism work-flows.
Common Feature Set:
The Collection Set Data module is designed to handle information on sites, collection/isolates and tissue samples using an interface that has a common appearance for each of these collection types. The Collection Data Set—Functional Design is found in Appendix 3 and represents the relationships to handling of tissue grinding, vouchers, taxonomy alternatives, and microorganism source material samples. The common feature set is described below followed by modifications for the special requirements each workflows.

| | |
|---|---|
| Site Data Form | collection site documentation for terrestrial or marine sites |
| Collection Data Form | (listed tab-forms) |
| Taxonomy | collection/isolate record for taxonomically distinct organisms |
| Biology/Ecology | documents specifics of the organism collection |
| Sample | for tracking one or many tissues samples that arise from one organism, and their grinding. |
| Voucher | for tracking many vouchers for one organism |
| Control | for tracking collectors and audit of data entry |
| Photos | extended photo handling, links one or many photos for each collection/isolate |

Map Form for viewing the collection sites and navigating the system, imbedded access to the map is found on the Site and Collection forms by single mouse click on the map.
Modifications to Common Feature Set for Plants
Collection Data Form
Ethnobotany (added tab) for documentation, uses NCI format
Modifications to Common Feature Set for Marines
   none
Modifications to Common Feature Set for Microorganisms
Source Material Data Form (added form) for one or many Source Materials collected from each Site, arranged by type: soil, non-soil, organism, corresponding collection

| Collection Data Form | |
|---|---|
| Growth | (replaces Biology/Ecology) to track growth under artificial culture conditions for one isolate |
| Sample | for fermentation of the isolate using many different protocols at many different times. |
| Archive | (replaces Voucher) for cryo-preservation of many labeled preserves for one isolate |

Working with Collection Set Data Module
Site Data Form
Numbering of site records is based upon the Utilities | Setup preference settings
Set Date uses dialog
Entry format for Latitude-Longitude position is based upon the Utilities | Setup preference settings, uses dialog
Set Habitat calls dialog
Set Collectors calls dialog
Entered by and Last Modified by are populated based on the system login
Map is opened with single-click on vicinity map
Collection Data Form
Taxonomy
Taxonomy entry uses table-lookups. Allows entry of genus name and back-population of higher taxonomy data where all above fields are blank. Allows entry of names not contained in the lookups from Family down
Save Taxonomy saves the determination to a related table for later searches
Other ID's views past taxonomy determinations
Morphology provides phylum-specific choices, editable through Utilities | Lookup Image display as BLOB field (*.bmp=100 kb)
Biology/Ecology
Change Habitat to modify the auto-populated Habitat Data from Site for a specific collection, uses dialog
Set Color calls dialog for entry of data-controlled color communication. Based on the Pantone Color Communication Standards
Growth (micro)
Set Media from lookup, for culture plating
View media calls descriptive dialog
Set Color calls dialog for entry of data-controlled color communication. Based on the Pantone Color Communication Standards
Sample (plant and marine)
Handles many samples for each taxonomically distinct collection, e.g. fruits, roots, bark.
Edit lookup values in Main Menu | Utilities
Monitored Bulk wt. set value
Grind weight controlled through Work Order
Sample (micro)
New Sample calls dialog for controlled entry—requires established Work Order
'Isolates for Fermentation'
View media calls descriptive dialog
View Protocols calls descriptive dialog
Voucher (plant and marine)
Tracks vouchers by number of replicates only—and not with individual tracking numbers
Print Herbarium/Collection Label
Archive (micro)
Assigns discreet 'Micro Archive Label' for each vial stored—table also stores collection/isolate ID, displays only those vials that have not been used
Ethnobotany (plant)
Based directly on NCI data model, handles many records for 'medicinal use' and 'local names' for each collection
Control
Display of audit information for Collections and associated Site or Microorganism Source Material Data
Photos
Link and display of many photos for each collection.
Displays image files—not BLOB fields.
Set path to directory, file server, or CDROM.
Stores metadata.
SAMPLE HANDLING
Feature Set:
The Sample Handling Module is query-driven and is editable.
Inventory, Submit, Receive (ISR) is the work-flow for querying the dataset, and formally submitting and receiving quantities of sample materials with different organizations at all stages of processing. Both transfer files and Archive records are created. Packing slips can be printed and dynamic digital export files created.
Design of this Module is based on the concept of chemical diversity=biological+geographic diversity, see Appendix 4, and proving the profiles of sample sets.
   Collection/Isolate (Inventory only)
   Voucher Specimens
   Microorganism Source Materials
   Microorganism Cryo Preserves
   Tissue Samples (field)
   Tissue Samples (lab)
   Crude Extracts
   Extract Fractions
   Purification Fractions
   Compound Purification
   Microtiter Plates
Work Orders (WO) is the work-flow for querying the dataset for formal submittal of sample materials at the different stages of internal processing. Work Order Archive records are created in within the NAPIS tables. Reports can be printed for directing work within the laboratory.

Tissue Samples for Grinding
Source Materials for Culture Plating
Isolates for Fermentation
Tissue Samples for Extraction
Extracts for Fractionation
Fractions for Purification
Pure Compounds for Structural Elucidation
Microtiter Plate Preparation Working with ISR For each Submittal and each Receive an archive record is written to the c:\napis\data\INTERMEDIATE_RECORD table (PK=i_rcd_id, system generated) and a corresponding record is written to the c:\napis\data\LAB_MATERIAL_BANK table (PK=lab_bank_label, system generated). The two tables are synchronized on i_rcd_id and is default set to '1' for this beta (can be reset by a table restructure in Paradox); the lab_bank_label value can be set in the c:\napis\system\NEXT_NUM table and is intended for use in labeling containers (e.g. vials) that store sample materials. This design presents technical challenges for migration of legacy datasets into NAPIS.

Of special note: Query Preferences are set at the Inventory Form menu-bar Query | Preferences form which define the columns in the dynamic grid, however, a preset list of query choices is displayed in the 'Query Builder'; the 'Query Preferences' define the 'Available Fields' choices in the Submit Form menu-bar Submit | Export File Preferences.

Inventory

Menu-bar

File | Open Inventory File calls dialog that shows metadata on prepared Inventory files, and allows users to browse to other computers to view other desktop-stored (and not server-stored) files. Files are stored either as *.db's or as queries. File | Open File calls a 'Browse' dialog that filters on *.db and opens the contents of that file dynamically.

Query | Preferences calls the 'Query Fields Preference' dialog. 'Query Result Fields' choices define the columns in the dynamic grid—and define the 'Available Fields' in the Submit Form menu-bar Submit | Export File Preferences.

Query | Define and Run Query calls the 'Query Definition' dialog. Build an SQL query by double-clicking on 'Fields'—single-click on operators—double-click on 'Values'—and select 'Run Query' to execute. Queries can also be manually entered in the window.

Query | Show SQL calls dialog that displays query statement

Tools

Pie calls a 'Pie Chart' that is dynamically created based on the selected grid column and grid dataset. Allows for select of any column—but may error if the dataset is too large.

Map calls the ISR-specific Map and dynamically displays the site points for lat-long values in the grid. Can overlay other stored site points from the SITE_COMMON table, or add additional GIS data layers.

To Submit calls the Submit Form, and prompts the user to save the file.

Submit

Menu-bar

File | Open Inventory calls a dialog that shows metadata on prepared Inventory files, and allows users to browse to other computers to view other desktop-stored (and not server-stored) files. Files are stored either as *.db's or as queries. File | Open Archive calls a dialog that displays past submittals written to the INTERMEDIATE_RECORD Submit Export File Preferences allows users to choose data columns for selective output of digital files and 'Packing Slips'

Tools

'Submit' calls the 'Create Submit Transmittal Record' dialog for setting 'Transmittal ID' and other address-related information. Selecting 'OK' here makes a transaction with the database at the c:\napis\data\INTERMEDIATE_RECORD table and the c:\napis\data\LAB_MATERIAL_BANK table.

Pie calls a 'Pie Chart' that is dynamically created based on the selected grid column and grid dataset. Allows for select of any column—but may error if the dataset is too large.

Map calls the ISR-specific Map and dynamically displays the site points for lat-long values in the grid. Can overlay other stored site points from the SITE_COMMON table, or add additional GIS data layers.

Receive

The Receive work-flow checks for uniqueness of sample_id in the LAB_MATERIAL_BANK table which is and important consideration for design of the Chemistry Module—which is sample_id (for tissue samples) driven. Non-unique values are displayed to the user and can be changed; the original sample_id values, however, are written to the original_sample_id field in the INTERMEDIATE_RECORD table and are not lost. In addition, where non-tissue sample materials are received (e.g. crude extracts or compounds) a placeholder record is written to each of the two synchronized tables with a type "T" to drive the Chemistry Module.

Menu-bar

File | Open Receive File calls a 'Browse' dialog that filters on *.db and opens the contents of that file dynamically.

File | Open Archive calls a dialog that displays past receives written to the INTERMEDIATE_RECORD Tools 'Receive' calls the 'Create Receive Transmittal Record' dialog for setting 'Transmittal ID' and other address-related information. Selecting 'OK' here makes a transaction with the database at the c:\napis\data\INTERMEDIATE_RECORD table and the c:\napis\data\LAB_MATERIAL_BANK table.

Pie calls a 'Pie Chart' that is dynamically created based on the selected grid column and grid dataset. Allows for select of any column—but may error if the dataset is too large.

Map calls the ISR-specific Map and dynamically displays the site points for lat-long values in the grid. Can overlay other stored site points from the SITE_COMMON table, or add additional GIS data layers.

Working with WO

For each Work Order created a record is written to the WORK_ORDER_DETAIL and WORK_ORDER tables, and a transaction is made with the LAB_MATERIAL_BANK where quantities are subtracted.

Menu-bar

File | Open Inventory calls a dialog that shows metadata on prepared Inventory files, and allows users to browse to other computers to view other desktop-stored (and not server-stored) files. Files are stored either as *.db's or as queries.

File | Open Archive calls a dialog that displays past receives written to the WORK_ORDER and WORK_ORDER_DETAIL tables Query | Define and Run Query calls the 'Query Definition' dialog. Build an SQL query by double-clicking on 'Fields'—single-click on operators—double-click on 'Values'—and select 'Run Query' to execute. Queries can also be manually entered in the window. 'Available Fields' are preset for Work Orders.

Query | Show SQL calls dialog that displays query statement

Query | Print Work Order prints a report for the displayed grid values

Tools
View Protocol calls a dialog for viewing available protocols (set at Utilities | Protocols)
Set Values calls a dialog for setting editable grid values
Submit calls a dialog for setting Work Order ID and date
CHEMISTRY
Feature Set:
The Chemistry feature is editable.
Sample Processing where tab-forms are marked with an *, NAPIS is conceptually based only on transactions with the database that directly involve material sample quantities. Processing protocols are noted with each transaction. The table containing * data is denormalized and is treated as an electronic notebook from the database security perspective, see Appendix 5.

| | |
|---|---|
| Extraction* | Crude Extracts quantity values |
| Fractionation* | Extract Fractions quantity values |
| Purification* | Purification Fractions quantity values |
| Compounds* | Compounds quantity values |
| Structural Elucidation* | Materials submitted for structural elucidation that are not recovered |
| Structure | ISIS/Base Sample specific compound structure information with ISIS/Base text-field data. Maintenance of these data are outside NAPIS and require ISIS/Base and ISIS/Draw from MDL Information Systems, Inc.. |
| ISIS/Base | ISIS/Base text-field data. |

Sample Characterization is a dedicated form for custom data fields and is not implemented at this beta—but is planned for the version release
ISIS/Base Chemistry is a copy of the tab-forms from Sample Processing that displays the entire ISIS database, and not just information that is Tissue-Sample specific. Browse is implemented for beta 1 but other query and substructure searching is not.

| | |
|---|---|
| Structure | ISIS/Base Sample specific compound structure information with ISIS/Base text-field data. Maintenance of these data are outside NAPIS |
| and require | |
| | ISIS/Base and ISIS/Draw from MDL Information Systems, Inc.. |
| ISIS/Base | ISIS/Base text-field data. |

Working with Chemistry Module
The Chemistry Module is sample_id driven, meaning that entry into the form requires selection of a value in the 'Select Sample No' dialog. The sample_id must be unique within NAPIS.
Records are inserted into the Chemistry Module with specific reference to the Work Order used to post the transaction with the LAB_MATERIAL_BANK.; this function makes the material sample available for entry into the Chemistry Forms. Record transactions are not posted until leaving the Chemistry Form, at which time they are posted to both the CHEMISTRY table and to the LAB_MATERIAL_BANK, creating an archive record (Electronic Notebook concept compliant) and a material quantity record, respectively.
Bioactivity data are display only and are shown in the middle and lower form fields (typical). The purpose in tracking Bioactivity here is to show that 1) activity is accounted for, and 2) that activity is conserved. Bioactivity data are written to the BIOACTIVITY table by the organization-specific LIMS (Laboratory Information Management System) and requires customization at the Database Administrator level. NAPIS does not contain LIMS functionality.

Chemistry Sample Processing Form
General
Entered By and Modified By display fields are name and date stamps in the CHEMISTRY table that are system generated based on the login and current date.
Tools
Insert Records calls dialog for entry of records that populate the upper grid on the form
View Protocols calls the dialog for viewing protocols (editable at Utilities | Protocols)
View Activity calls a dialog the displays the contents of the BIOACTIVITY table Submittal calls a dialog for navigation to 'Sample Handling' forms and corresponding data that tracks the transfer of the sample materials.
Extraction
Extract Numbers are composites with a prefix—sample_id—suffix (e.g. FA, DM, DMH)
Records are inserted through the 'Insert Extraction Records' dialog and are Work Order specific. The '# of Extracts' entry tells the system how many records to insert. The actual Suffix, Tissue Wet Wt and Yield values are edited at the grid. Non-editable grid cells have a yellow background.
Fractionation
Fraction Numbers are composites with a Extract No—suffix (e.g. 1–30)
Fraction records displayed in the upper grid are Extract No specific, only those fractions that correspond to the grid-selected Extract No on the Extraction tab-form are displayed.
Records are inserted through the 'Insert Fractionation Records' dialog and are Work Order specific. The '# of Fractions' entry tells the system how many records to insert. The actual Suffix, Extract Wt and Yield values are edited at the grid.
Non-editable grid cells have a yellow background.
Purification
Purification Numbers are entered one at a time in the 'Set Purification Values' dialog
Purification fraction records displayed in the upper grid are Sample No specific, all Purification fractions for the selected Sample No are displayed.
Records are inserted through the 'Insert Purification Values' dialog and are Work Order specific. 'Pooled Fractions' can be selected from 'Available Fractions' with a many-to-many relationship. The actual Material Wt and Yield values are edited at the grid. Non-editable grid cells have a yellow background.
Compound
Compound Numbers are entered one at a time in the 'Set Compound Values' dialog
Compound records displayed in the upper grid are Sample No specific, all Compounds for the selected Sample No are displayed.
Records are inserted through the 'Insert Compound Values' dialog and are Work Order specific. 'Pooled Fractions' can be selected from 'Available Fractions' with a many-to-many relationship. The actual Material Wt and Yield values are edited at the grid. Non-editable grid cells have a yellow background.
Structural Elucidation
StructE Numbers are entered one at a time in the 'Structural Elucidation' dialog StructE records displayed in the upper grid are Sample No specific, all 'Material ID' and 'Material Types' (E, F, P, C) for the selected Sample No are displayed.
StructE records are posted only to the CHEMISTRY table, based on the assumption the these samples are consumed and depleted by the process.

Structure
Displays 2d compound structure for the many structures known for a given Sample No, along with other ISIS/Base text-field data. Not searchable at this time.
ISIS/Base
ISIS/Base text-field data known for a given Sample No that corresponds directly to the Structure selected. Not searchable at this time.
ISIS/Base Chemistry Form
Structure
Displays 2d compound structure for the all structures in the ISIS database, along with other ISIS/Base text-field data. Not searchable at this time.
ISIS/Base
Displays ISIS/Base text-field data known for a given Sample No that corresponds directly to the Structure selected. Not searchable at this time.
Planned for the version release are text-field query and substructure-based query tools.
GIS
Feature Set:
The ArcView GIS feature provides advanced query power for performing GIS grid analysis and is called from the GIS Module selection. The GIS feature is a DDE call to the ESRI desktop GIS software ArcView, and is different from the MapObject that is native to NAPIS.
The NAPIS Map is embedded within the NAPIS program and provides a custom user interface for performing GIS spatial analysis. The map is called from within the Collection Set Data Module, the PSDE Module, and within the Sample Handling Module at ISR
Working with GIS
This function calls the Customized ArcView Program that is booted from the Main Menu | GIS selection. Discussion is not included here, refer to the ArcView documentation (limited test sites).
Working with the NAPIS Map
GIS spatial analysis query using the NAPIS Map is powerful and requires two-stages. In the first stage, the Site points are selected using one of three general methods:
    double-click on 'Selected' value in Map Grid
    GIS spatial analysis query for points in polygon using: Query| Spatial Analysis against map layer; or polygon tools for irregular, rectangle, circle, radius-point polygons
    traditional text-field query against sites using Query | Site Query.
In the second stage, an attribute query is run against the traditional text-field tables linked to the selected sites for:
Collections/Isolates
Microorganism Source Materials
Microorganism Cryo-Preserves
Tissue Samples
Crude Extracts
Extract Fractions
Purification Fractions
Pure Compounds
Menu bar
Map | Export Map saves map as bitmap (*.bmp) file
Map | Print Map sends displayed map to printer
Map | Print Grid sends displayed grid to printer
Folder | New creates new folder and calls 'Folder Properties' dialog (below).
Folder | Open opens Folder, can have many folders stored for different projects
Folder | Close closes Folder
Folder | Set Extents as Default allows the displayed map extents to be saved as the Folder default setting.
Folder | Properties Define map extents and map layer profile through Add, Remove.
Define map layer properties for Path, ID field. GIS file type, Symbol Style, and layer Color.
View | Zoom various zoom tools, self explanatory
View | Move various move tools, self explanatory
View | Display Settings for setting appearance of Area Inset, Legend, Scale Bar, and Selection Grid on the main map screen view
Tools | Zoom In zooms to drawn rectangle
Tools | Zoom Out zooms out incrementally
Tools | Pan pan over map surface (pan also available at Area Inset by moving the red box)
Tools | Information calls dialog to display text-field attributes of selected map feature—active layer specific
Tools | Measure enables measure tool double-click to end measure
Tools |Map Tip enables fly-by label of active-layer specific feature that the cursor is passed over in the map display
Tools | Navigate enables left-click on Site point for pull-down choice box allowing navigation to other forms in the system and displays site-specific record choices (always available with right-click)
Tools | Find finds a map feature by the attribute text value for selected map-layer, and flashes the feature on the map. Zoom-to and Pan-to functions.
Query | Spatial Query calls 'Spatial Query Definition' dialog that allows users to define an area polygon for a selected map-layer to select Site points that fall within that area polygon. Extended SQL query functionality. Query result displayed in printable dialog.
Query | Site Query calls 'Query Definition' dialog and provides SQL functionality for query of Sites. Query result displayed in printable dialog.
Query | Attribute Query calls 'Query Definition' dialog through choice list with pre-selected 'Available Fields' that are "query area" specific. Sets all 'Site Selected' column values to true in Grid. Query result displayed in printable dialog.
Tool bar
Back arrow back to previous form
Print print screen
Folder Properties calls 'Folder Properties' dialog (above)
Select Active Layer list box choice of active layer—affects query, tip
Zoom In zooms to drawn rectangle
Zoom Out zooms out incrementally
Pan pan over map surface (pan also available at Area Inset by moving the red box)
Information calls dialog to display text-field attributes of selected map feature—active layer specific
Measure enables measure tool double-click to end measure
Tip enables fly-by label of active-layer specific feature that the cursor is passed over in the map display
Find Feature finds a map feature by the attribute text value for selected map-layer, and flashes the feature on the map. Zoom-to and Pan-to functions.
Zoom to Selected zooms to selected map feature
Zoom to Active Layer zooms to extents of active layer
Zoom to Extents zooms to project-set default extents
Move West
Move East
Move North
Move South
Select Site by Polygon allows users to define an area irregular polygon for a selected map-layer to select Site points that fall within that area polygon. Turns selected Site points yellow and sets 'Selected' value from "false" to "true" in map Grid, and makes selected set available for Menu bar Query | *.

Select Site by Rectangle allows users to define an rectangle polygon for a selected map-layer to select Site points that fall within that area polygon. Turns selected Site points yellow and sets 'Selected' value from "false" to "true" in map Grid, and makes selected set available for Menu bar Query | *.

Select Site by Circle allows users to define a circle by dragging for a selected map-layer to select Site points that fall within that area polygon. Turns selected Site points yellow and sets 'Selected' value from "false" to "true" in map Grid, and makes selected set available for Menu bar Query | *.

Select Site by Radius-point allows users to define a circle by defining the radius distance (in map degrees) for a selected map-layer to select Site points that fall within that area polygon. Turns selected Site points yellow and sets 'Selected' value from "false" to "true" in map Grid, and makes selected set available for Menu bar Query | *.

Clear Selected Sites sets 'Selected' value from "true" to "false" in map Grid Selected to Top moves 'Selected' value="true" records to top of Grid list.

Sort Ascending sorts ascending on 'Site_id'
Sort Descending sorts descending on 'Site_id'
Navigate enables left-click on Site point for pull-down choice box allowing navigation to other forms in the system and displays site-specific record choices (always available with right-click)

REPORTS

Feature Set: The Reports feature requires customization by the program-specific Database Administrator using a third-party tool (Crystal Reports).

For other query functionality see Sample Handling | ISR and the NAPIS Map discussions.

Working with Reports Module

The purpose of this Module is to provide a link to existing and different LIMS (Laboratory Information Management System) in place at the different organizations. The NAPIS Data model is designed to link to the different LIMS systems using primarily:

material_id VARCHAR2(20) in LAB_MATERIAL_BANK and PLATE_DETAIL tables

Other tables can be exposed with Crystal Reports for DBA generated custom reports.

UTILITIES

Feature Set:
The Utilities feature is editable.
Setup is to set the system level functions for: Lat-Long entry, ArcView GIS path, station id, and numbering
Lookup Tables provides maintenance for system lookup table values
Protocols is for entry of protocol descriptions and bitmap images
Media is for entry of microorganism growth media descriptions
Personnel is to manage system persons, users, collectors, and investigators
Companies is to manage company address information
Working with Utilities Module
This Module is designed for system maintenance with work-flows in the above-listed areas. Users will find these functions to be typical and self explanatory.

Turning now to FIG. 8, illustrated therein is a block diagram representing the data modeling concepts process of the present invention. Of particular note is the arrangement of the collection set data (upper half) into three horizontal tiers for marine, plant, and microorganism, and into three vertical columns for site, collection/isolate (taxonomically distinct) and tissue sample. This functional arrangement is directly reflected in the design of the NAPIS Collection Set Data module. The Chemistry data (lower half) illustrates the technical challenges for chemistry sample processing and, more particularly, the many-to-many relationships between fractionation, purification, and structural elucidation. Implied is the need for Sample Handling.

FIG. 9 is a block diagram representation of the Collection Set Data process, illustrating the physical entity relationships. More particularly, this figure shows the physical design of the entity relationship model formed in accordance with the present invention. Included therein is the normalized table structure for N_Collect_Commmon and its related tables.

FIG. 10 is a block diagram representation of the activity directed isolation sample handling process formed in accordance with the present invention. The functional design has an emphasis on chemistry (center column). The NAPIS elements are acquisition, chemistry and dereplication. Links to other outside elements are shown in oval, including the substructure searches, structures, and LIMS (laboratory information management system). Activity directed isolation is an iterative process of discovery where extracts are tested for activity in a bioassay (LIMS), and a decision is made to fractionate based on the bioassay results "D." Fractions are then sent for bioassay, and "D" actives are put through isolation and likewise through structural elucidation.

At each step, additional wild-biomass material may be required from Acquisition. dereplication is performed at one or more of each of the chemistry processing stages using NAPIS PSDE linked to third-party databases. Determined structures are handled by a third-party software. Bioassay is handled by a third-party LIMS. Thus, the NAPIS Sample Handling module design is based on this functional representation.

Shown in FIG. 11 is a block diagram representation of the Sample Handling process. This diagram shows the Physical Entity Relationships based on the entity relationship model of the present invention. Shown therein are, among other things, the table structure for LAB_MATERIAL_BANK and INTERMED_RECORD, and related tables.

FIG. 12 shows the physical entity relationships of the Chemistry/Bioactivity process of the present invention. Shown therein is the D-normalized table structure for the Chemistry table, and other related tables.

VII. Summary

The high throughput screening of the present invention. For natural products acquisitions addresses two general requirements—recollection and dereplication. The present invention offers key features for (a) linking to commercially available data, (b) linking to digitally stored specimen photographs, (c) standardizing entry/capture protocols, and (d) GIS capability. It further provides a customized user interface that integrates traditional database functionality with links to other databases, and image capture/editing and GIS capabilities. The operating system and language provides support for seamless integration of these computer functionalities.

In addition to tracking the collections of natural products source organisms, information handling of the present invention plays an important role in natural resource stewardship. It assembles information on known chemistry and natural resources for planning and tracking collections, functioning like a biodiversity inventory. In addition, harvesting the chemically diverse resources of a country requires a collecting permit, and the permit process includes a review of the planning and monitoring steps. The permit review process requirements are a logical extension of the planning and tracking requirements. It is conceivable that the information and information handling of the present invention can be used to leverage collecting permit opportunities.

Screening natural products extracts, however, is expensive when compared with synthetic and combinatorial chemical libraries. Biological activity directed isolation studies and structural elucidation of unknown compounds adds to the expense. Acquiring and tracking natural products source organism collections have extended requirements for information handling. Combining these requirements within the system of the present invention not only reduces their costs, but provides the leverage to convert them to assets for guiding future efforts.

The embodiments of the invention in which an exclusive property or privilege is claimed are defined as follows:

1. A computer-implemented system for processing natural products information, the natural products information, including natural products data and natural products images, the system comprising:
   (a) Computer processing means for processing data;
   (b) Memory means for storing data on a storage medium;
   (c) Display means for displaying data;
   (d) Means for processing natural products data in a standard format;
   (e) Means for processing natural products images and correlating said natural products images with said natural products data; and
   (f) Means for correlating said natural products data and natural products images with remote databases to form correlated data for storage in said memory means and for display to a user on said display means.

2. The system of claim 1, wherein said correlating means further comprises means for correlating said natural products data and said natural products images with a taxonomic structure.

3. The system of claim 2, wherein said correlating means includes means for correlating remote databases based on one of either genus species (as a paired index), Chemical Abstracts Registry Number, or the National Oceanographic Data Center Taxonomic Code (or Serial No.).

4. The system of claim 2, wherein said correlating means is configured to correlate said natural products data and said natural products images with Geographical Information Systems.

5. The system of claim 1, wherein said processing means for said natural products data and said processing means for said natural products images includes handling of digital images.

6. The system of claim 1, wherein said correlating means includes a graphical user interface.

7. A data processing system for managing a configuration of natural products inventory, comprising:
   (a) A computer processor means for processing data;
   (b) Storage means for storing data;
   (c) First means for processing natural products data in a standard format;
   (d) Second means for processing natural products image data and correlating said natural products image data with said natural products data;
   (e) Third means for correlating data regarding said natural products image data and said natural products data with remote databases.

8. The system of claim 7, wherein said third means for processing data further comprises means for correlating said natural products data and said natural products image data with a taxonomic structure.

9. The system of claim 8, wherein said third means for processing data includes a graphical user interface.

10. The system of claim 8, wherein said third means for processing data is configured to correlate natural products data and natural products image data with geographical information systems.

11. The system of claim 7, wherein said second means for processing natural products image data includes handling of digital images.

12. The system of claim 7, wherein said third means for processing data further comprises means for correlating remote databases with said natural products data based on one of either genus species (as a paired index), Chemical Abstracts Registry Number, or the National Oceanographic Data Center Taxonomic Code (or Serial No.).

* * * * *